United States Patent [19]

Bouchaudon et al.

[11] Patent Number: 4,916,119
[45] Date of Patent: Apr. 10, 1990

[54] PEPTIDES, THEIR PREPARATION AND COMPOSITIONS CONTAINING THEM

[75] Inventors: Jean Bouchaudon, Morsang-sur-Orge; Daniel Farge, Thiais; Claude James, Paris, all of France

[73] Assignee: Rhone-Poulenc Industries, Paris, France

[21] Appl. No.: 163,878

[22] Filed: Jun. 27, 1980

[30] Foreign Application Priority Data

Jun. 29, 1979 [FR] France ................... 79 16844

[51] Int. Cl.$^4$ .................. C07K 5/08; C07K 5/10; C07K 37/02
[52] U.S. Cl. ................... 514/18; 530/330; 530/331; 530/332
[58] Field of Search ............... 260/112.5 R; 424/177; 514/18; 530/331, 2, 330

[56] References Cited

U.S. PATENT DOCUMENTS 4,311,640   1/1982   Kuroda et al. ............... 260/112.5 R

FOREIGN PATENT DOCUMENTS 0011283   5/1980   European Pat. Off. ...... 260/112.5 R
0013856   6/1980   European Pat. Off. ...... 260/112.5 R

OTHER PUBLICATIONS

Life Sciences, vol. 26, pp. 883–888, Jan. 17, 1980.
C. R. Acad. Se. Paris, 1.289, (Sep. 24, 1979).
Comptes Rendus Hebdomandaires Des Seames De L'Academié Des Sciences Paris, pp. 1320–1304, (1965).
Bulletin de la Societe de Chimie Biologigie, 1967, 49, No. 11, pp. 1579–1591.
Agricultural and Biological Chemistry, 41,(5), 763–768, 1977.
11th Internat'l Congress of Chemotherapy 19th Interscience Conference on Antimicrobial Agents & Chemitherapy, (1979).
Biochem- and Biophys. Res. Commun. 59, 1974, 1317–1325.
Biochemistry, vol. 9, No. 4, 1970, 823–831.

Primary Examiner—Delbert R. Phillips
Assistant Examiner—F. T. Moezie
Attorney, Agent, or Firm—Stevens, Davis, Miller & Mosher

[57] ABSTRACT

Tripeptides of the general formula:

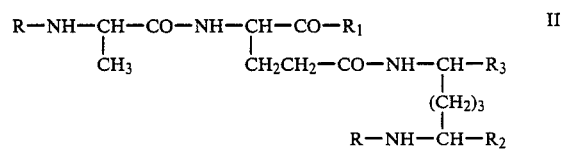

wherein the symbols R, which may be the same or different represent hydrogen or a fatty acid residue (at least one of them representing a fatty acid residue), $R_1$ represents hydroxy, amino or alkoxy and $R_2$ and $R_3$, which may be the same or different, represent hydrogen, carboxy, carbamoyl or alkoxycarbonyl radical (with the proviso that $R_2$ and $R_3$ cannot simultaneously represent a hydrogen atom), the alanine moiety being in the L form, the glutamic acid moiety being in the D form, the lysine moiety (when $R_2$ or $R_3$=a hydrogen atom) being in the L form and the 2,6-diaminopimelic acid moiety or its derivatives (when $R_2$ and/or $R_3$=carboxy, carbamoyl or alkoxycarbonyl) being in the D,D, L,L, D,D/L,L (racemic) or D,L (meso) form, and salts thereof, possess immunological adjuvant and immunostimulant activity.

10 Claims, No Drawings

PEPTIDES, THEIR PREPARATION AND COMPOSITIONS CONTAINING THEM

DESCRIPTION

The present invention relates to new tripeptides which possess immunostimulant activity, to their preparation and to compositions containing them.

Bacterial walls, e.g. The walls of mycobacteria, essentially consist of a peptapoglycan, formed from N-acetylmuramic acid, to which peptides containing the sequence L-Ala-D-Glu-DAP are fixed: Ala represents alanine, Glu represents glutamine and DAP represents diaminopimelic acid. Furthermore, bacterial walls are very rich in lipids, some of which are free and can be extracted and others of which are bonded to the structure of the wall and comprise mycolic acids ($\alpha$-branched and $\beta$-hydroxylic giant fatty acids). The constituents of the cell wall together form a covalent structure composed of a peptidoglycan and of an arabinogalactan mycolate, which are bonded to one another by means of phosphodiester linkages. These bacterial walls possess most of the biological properties of whole cells when they are associated with a mineral or vegetable oil and administered after being suspended in physiological solution.

Peptides, coupled with N-acetylmuramic acid, which contain the sequence L-Ala-D-Glu or L-Ser-D-Glu (in which Ser represents serine) and which are effective as immunological adjuvants and as anti-infectious agents are described in British patent specification Nos. 1496332 and 1496333 and in Belgian patent specification Nos. 852,348 and 852,349.

Products which result from the coupling of a fatty acid with a heptapeptide saccharide isolated from a mycobacterium containing a "D" wax, and which can be represented by the following formula:

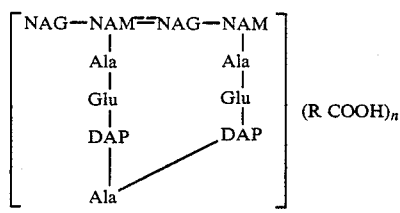

wherein, in particular, NAG represents N-acetylglucosamine, NAM represents N-acetylmuramic acid and R represents an alkyl radical containing 9 to 17 carbon atoms, are described in British patent specification No. 1,525,763. These products are immunological adjuvants for the production of antibodies and the potentiation of delayed hypersensitivity, which are capable of acting alone, i.e. it is not necessary to administer them in oily solution.

All these products are characterised by the presence of N-acetylmuramic acid, which, according to Kasumoto et al., Tetrahedron Letters, 49, 4,899 (1978), is considered to be associated with the immunological activity.

It has now been found that certain other tripeptides possess remarkable adjuvant and immunostimulant properties, despite the absence of N-acetylmuramic acid. Furthermore, these compounds, which are well defined, can easily be obtained with the purity required for therapeutic use.

The present invention accordingly provides tripeptides of the general formula:

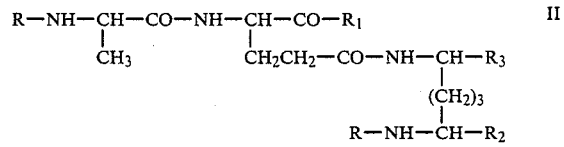

wherein the symbols R, which may be the same or different, represent a hydrogen atom or a fatty acid residue, at least one of the symbols R representing a fatty acid residue, $R_1$ represents a hydroxy or amino radical or an alkoxy radical in which the alkyl moiety contains 1 to 4 carbon atoms and is optionally substituted by a phenyl or nitrophenyl radical, and the symbols $R_2$ and $R_3$, which may be the same or different, represent a hydrogen atom, a carboxy or carbamoyl radical or an alkoxycarbonyl radical in which the alkyl moiety contains 1 to 4 carbon atoms and is optionally substituted by a phenyl or nitrophenyl radical, it being understood that the symbols $R_2$ and $R_3$ cannot simultaneously represent a hydrogen atom, and that, in general formula II, the alanine moiety is in the L form, the glutamic acid moiety is in the D form, the lysine moiety, when one of the symbols $R_2$ or $R_3$ represents a hydrogen atom, is in the L form, and the 2,6-diaminopimelic acid moiety or its derivatives, when the symbols $R_2$ and $R_3$, which may be the same or different, represent a carboxy, carbamoyl or alkoxycarbonyl radical, are in the D,D, L,L, D,D/L,L (racemic) or D,L (meso) form, and salts thereof.

By term fatty acid residue as used in this specification and the accompanying claims is means an alkanoyl radical containing 1 to 45 carbon atoms (which is optionally substituted by a hydroxy, phenyl or cyclohexyl radical), an alkenoyl radical which contains 3 to 30 carbon atoms and may contain more than one double bond, or a mycolic acid residue, such as that encountered in the structure of the bacterial wall of mycobacteria, Nocardia or Corynebacteria.

It is to be understood that, in this specification and the accompanying claims, alkyl radicals and alkyl moieties of alkoxy, alkocycarbonyl and alllkanoyl radicals, and alkenyl moieties of alkenoyl radicals, may be straight- or branched-chain.

According to a feature of the present invention, the tripeptides of general formula II can be obtained in accordance with the methods generally used in peptide synthesis. The various reactions are carried out after the blocking, by means of suitable protecting groups, of the amino or carboxylic acid groups which must not participate in the reactions, and are followed by the unblocking of these groups.

More particularly, the tripeptides of general formula II are prepared by reacting a dipeptide of the general formula:

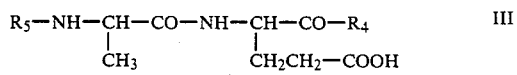

wherein $R_5$ represents a fatty acid residue or an amino-protecting group, e.g. The benzyloxycarbonyl or T-butoxycarbonyl radical, and $R_4$ represents an amino radical or an alkoxy radical containing 1 to 4 carbon atoms (which is optionally substituted by a phenyl or nitrophenyl radical), with an aminoacid of the general formula:

$$H_2N-CH-R_3 \atop \underset{R_5-NH-CH-R_2}{(CH_2)_3}$$  IV wherein $R_2$, $R_3$ and $R_5$ are as hereinbefore defined, at least one of the symbols $R_5$ in general formulae III and IV representing a fatty acid residue, followed, when one of the radicals $R_5$ represent an amino-protecting group by conversion, by known methods, of the amino-protecting group into a hydrogen atom, optionally followed, when the radical $R_4$ represents an alkoxy radical containing 1 to 4 carbon atoms which is optionally substituted by a phenyl or nitrophenyl radical, by conversion, by known methods, of the alkoxy radical into a hydroxy group, optionally followed, when one or both of the radicals $R_2$ and $R_3$ represent an alkoxycarbonyl radical in which the alkyl moiety contains 1 to 4 carbon atoms and is optionally substituted by a phenyl or nitrophenyl radical, by conversion by known methods, of te alkoxycarbonyl radical into a carboxy radical.

By the expression "known methods" as used in this specification and the accompanying claims is meant methods heretofore or described in the chemical literature.

In general, it is necessary to activate the free carboxylic acid group of the dipeptide of general formula III before it is reacted with the aminoacid of general formula IV. Preferably, the activated derivative of the dipeptide of general formula III is a mixed anhydride prepared in situ by reacting an alkyl halogenoformate (e.g. isobutyl chloroformate) with the dipeptide of general formula III. The reaction of the activated derivative of the dipeptide of general formula III with the aminoacid of general formula IV is generally carried out in an organic solvent, e.g. dioxan, tetrahydrofuran, chloroform, toluene or dimethylformamide, or in an aqueous-organic medium, in the presence of a base (an inorganic base, e.g. sodium hydroxide, or an organic base, e.g. triethylamine), at a temperature between $-10°$ and $+30°$ C.

The known methods used for the replacement, if appropriate, of the radical $R_5$ by a hydrogen atom, of the radical $R_4$ by a hydroxy radical and of the radicals $R_2$ and $R_3$ by a carboxy radical depend on the nature of the protecting groups. It is particularly advantageous to choose the radicals $R_2$, $R_3$, $R_4$ and $R_5$ so that their replacement by a hydroxy or carboxy radical, depending on the particular case, or by a hydrogen atom, can be carried out in a single stage. For this purpose, it is appropriate to choose as the radical $R_4$ a benzyloxy or nitrobenzyloxy radical and to choose as the radicals $R_2$, $R_3$ and $R_5$ a benzyloxycarbonyl or nitrobenzyloxycarbonyl radical. Under these conditions, the replacement of these radicals is carried out by hydrogenation, the reaction being carried out in a suitable organic solvent, e.g. acetic acid (if appropriate mixed with another solvent, e.g. methanol), or in an aqueous-organic solvent, in the presence of a catalyst, for example palladium, e.g. palladium-on-charcoal, at a temperature of the order of 20° C. and under a pressure of the order of 760 mm Hg.

The dipeptides of general formula III can be obtained by reacting an activated derivative of L-alanine, of the general formula:

$$R_5-NH-CH-COOH \atop CH_3$$  V wherein $R_5$ is an hereinbefore defined, with a D-glutamic acid derivative of the general formula:

$$H_2N-CH-CO-R_4 \atop CH_2CH_2-COOH$$  VI wherein $R_4$ is as hereinbefore defined, under the conditions described above for the reaction of a dipeptide of general formula III with an aminoacid of general formula IV.

The dipeptides of general formula III wherein $R_5$ represents a fatty acid residue can be obtained by reacting an activated derivative of a fatty acid of the general formula:

$$R'-C-OH$$  VII wherein $R'-C-$ represents a fatty acid residue as herein before defined, with a dipeptide of the general formula:

$$H_2N-CH-CO-NH-CH-CO-R_4 \atop \underset{CH_3 \qquad\qquad CH_2CH_2-COOH}{}$$  VIII wherein $R_4$ is as hereinbefore defined.

An acid halide or a mixed anhydride, which is generally prepared in situ by reacting an alkyl halogenoformate, e.g. isobutyl chloroformate, with the acid of general formula VII, in the presence of a base, is particularly advantageously used as the activated derivative of the acid of general formula VII.

If the acid of general formula VII is used in the form of an acid halide, more particularly the chloride, the reaction is generally carried out in an organic solvent, e.g. diethyl ether or methylene chloride, in the presence of a base (an inorganic base, e.g. sodium hydroxide, or an organic base, e.g. triethylamine), at a temperature from 0° to 30° C. The dipeptide of general formula VIII is generally used in the form of a salt, such as the hydrochloride.

If the acid of general formula VII is used in the form of a mixed anhydride, the reaction is carried out under the conditions described above for the reaction of a dipeptide of general formula III with an aminoacid of general formula IV. The dipeptide of general formula VIII is generally used in the form of a salt, e.g. The hydrochloride.

The aminoacid of general formula IV wherein $R_2$ represents a carbamoyl radical, $R_3$ represents a carboxy radical and $R_5$ represents a benzyloxycarbonyl radical, i.e. The (D)-monoamide of benzyloxycarbonyl-(D)-meso-2,6-diaminopimelic acid, can be prepared in accordance with the process described in British patent specification No. 1,496,332.

The aminoacid of general formula IV wherein $R_2$ represents a carbamoyl radical, $R_3$ represents a carboxy radical and $R_5$ represents a fatty acid residue or an amino-protecting group, in the racemic, D,D or L,L form, can be prepared from the corresponding 2,6-diaminopimelic acid. For this purpose, the benzyl ester of 2,6-dibenzyloxycarbonylaminopimelic acid is prepared by known methods and is mono-saponified in accordance with the technique described by A. Arendt et al., Roczniki Chemii Ann. Soc. Chim. Polonorum, 48, 1,305 (1974) [Chem. Abstr., 82, 31497 g (1975)], and the mono-saponified product is then converted, by reaction with ammoniacal methanol, into the monoamide of the general formula:

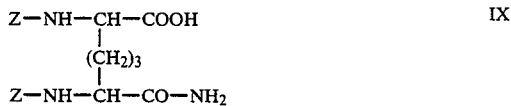

(wherein Z represents a benzyloxycarbonyl radical), which, after hydrogenation to convert the benzyloxycarbonyl radicals to hydrogen atoms in the presence of palladium-on-charcoal, yields 2,6-diaminopimelamic acid. By reacting a copper salt, such as cupric bromide or basic copper carbonate, with the 2,6-diaminopimelamic acid, a complex is formed which can be represented by the formula:

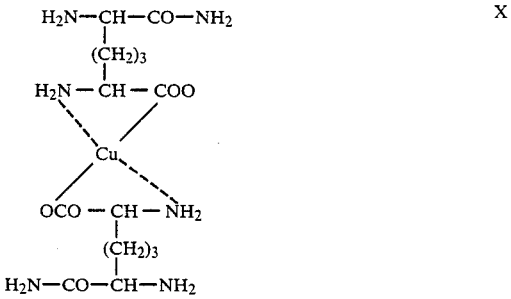

wherein the amino radical in the α-position to the carbamoyl group can be acylated by reaction with an activated derivative of an acid of general formula VII (preferably a halide, e.g. the chloride) or protected by reaction with an alkyl halogenoformate or a benzyl halogenoformate. The complex formed in this way is dissociated by reaction with hydrogen sulphide in order to give the aminoacid of general formula IV wherein $R_2$ represents a carbamoyl radical, $R_3$ represents a carboxy radical and $R_5$ is as hereinbefore defined.

The aminoacid of general formula IV wherein $R_2$ represents a carboxy radical, $R_3$ represents a carbamoyl radical and $R_5$ represents a fatty acid residue or an amino-protecting group, in the D,D, L,L, D,D/L,L (racemic) or D,L (meso) form, can be prepared from the corresponding 2,6-diaminopimelic acid. For this purpose, the copper complex of general formula X, wherein the amino radical in the α-position to the carbamoyl group can be protected by reaction with an alkyl halogenoformate or a benzyl halogenoformate, is prepared. The complex formed in this way is dissociated by reaction with hydrogen sulphide in order to give the aminoacid of general formula IV wherein $R_2$ represents a carbamoyl radical, $R_3$ represents a carboxy radical and $R_5$ represent an amino-protecting group. The amino radical in the α-position to the carboxy group can be protected by a fatty acid residue or by an amino-protecting group which is different from the protecting group $R_5$ which is already present. Removal of the protecting group originally represented by $R_5$ without affecting the newly introduced fatty acid residue or amino-protecting group yields a product of general formula IV wherein $R_2$ represents a carboxy radical, $R_3$ represents a carbamoyl radical and $R_5$ represents an amino-protecting group or a fatty acid residue.

The aminoacid of general formula IV wherein the symbols $R_2$ and $R_3$ may be the same or different and each represents a carboxy or carbamoyl radical or an alkoxycarbonyl radical in which the alkyl moiety contains 1 to 4 carbon atoms (and is optionally substituted by a phenyl or nitrophenyl radical) and $R_5$ represents a fatty acid residue or an amino-protecting group, in the D,D, L,L, D,D/L,L (racemic) or D,L (meso) form, can be prepared from an aminoacid of general formula IV wherein $R_2$ and $R_3$ are as hereinbefore defined and $R_5$ represents a hydrogen atom, by blocking one of the two amine groups in accordance with the method described by E. Bricas et al., Biochemistry, 9, 823 (1970) to permit the addition of a fatty acid residue or an amino-protecting group to one of the amine groups.

The aminoacid of general formula IV wherein the symbols $R_2$ and $R_3$ are different and represent a carbamoyl radical or an alkoxycarbonyl radical in which the alkyl moiety contains 1 to 4 carbon atoms (and is optionally substituted by a phenyl or nitrophenyl radical) and $R_5$ represents an amino-protecting group, in the D,D, L,L, D,D/L,L (racemic) or D,L (meso) form, can be obtained from an aminoacid of general formula IV wherein the symbols $R_2$, $R_3$ and $R_5$ are as hereinbefore defined and the amine group in the α-position to the symbol $R_3$ is protected by an amino-protecting group which is different from $R_5$, by removing this protecting group without affecting $R_5$.

The product of general formula IV, wherein the amine group in the α-position to the symbol $R_3$ is protected by an amino-protecting group, is obtained, after the esterification of a product of general formula IV wherein one of the symbols $R_2$ and $R_3$ represents a carboxy radical and the other represents a carbamoyl radical, by blocking the amine group by known methods.

The aminoacid of general formula IV wherein $R_5$ represents a fatty acid residue or an amino-protecting group and either $R_2$ represents a hydrogen atom and $R_3$ represents a carboxy or carbamoyl radical or an alkoxycarbonyl radical in which the alkyl moiety contains 1 to 4 carbon atoms (and is optionally substituted by a phenyl or nitrophenyl radical), or alternatively $R_2$ represents a carboxy or carbamoyl radical or an alkoxycarbonyl radical in which the alkyl moiety contains 1 to 4 carbon atoms (and is optionally substituted by a phenyl or nitrophenyl radical) and $R_3$ represents a hydrogen atom, can be prepared from lysine by known methods.

The L-alanine derivative of general formula V wherein $R_5$ represents a fatty acid residue can be obtained by reacting an acid of general formula VII or an activated derivative thereof with L-alanine, in which the carboxy group is protected, if appropriate, in the form of an ester, followed, if necessary, by the removal of the carboxy-protecting group.

If the carboxy group of the L-alanine is protected, the acid of general formula VII is generally condensed in the presence of a condensation agent, e.g. dicyclohexylcarbodiimide, the reaction being carried out in an organic solvent, e.g. methylene chloride or dimethylformamide, at a temperature from −10° to +30° C.

If the carboxy group of the L-alanine is free, it is necessary to activate the acid of general formula VII before it is reacted with the L-alanine. An acid halide or a mixed anhydride is particularly advantageously used as the activated derivative of the acid of general formula VII. The reaction is then carried out under the conditions described above for the reaction of an acid of general formula VII with the dipeptide of general formula VIII.

The dipeptide of general formula VIII can be obtained by condensing L-alanine, in which the amine group is protected, with D-glutamic acid, or a derivative thereof, by known methods employed in peptide chemistry, this reaction being followed by the removal of the amino-protecting group.

According to a further feature of the present invention, the tripeptides of general formula II are obtained by reacting an activated derivative of L-alanine, of general formula V, with a dipeptide of the general formula:

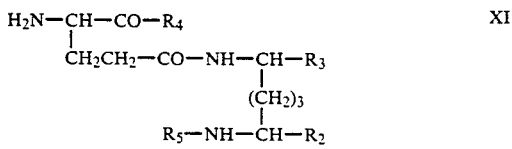

wherein $R_2$, $R_3$, $R_4$ and $R_5$ are as hereinbefore defined, it being understood that at least one of the symbols $R_5$ in formulae V and XI represents a fatty acid residue, under the conditions described above for the reaction of a dipeptide of general formula III with an aminoacid of general formula IV, followed, when one of the radicals $R_5$ represents an amino-protecting group by conversion, by known methods, of the amino-protecting group into a hydrogen atom, optionally followed, when the radical $R_4$ represents an alkoxy radical containing 1 to 4 carbon atoms which is optionally substituted by a phenyl or nitrophenyl radical, by conversion, by known methods, of the alkoxy radical into a hydroxy group, optionally followed, when one or both of the radicals $R_2$ and $R_3$ represent an alkoxycarbonyl radical in which the alkyl moiety contains 1 to 4 carbon atoms and is optionally substituted by a phenyl or nitrophenyl radical, by conversion by known methods, of the alkoxycarbonyl radical into a carboxy radical.

The dipeptide of general formula XI can be obtained by reacting a D-glutamic acid derivative of the general formula:

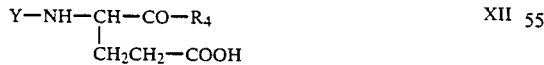

wherein $R_4$ is as hereinbefore defined and Y represents an amino-protecting group, e.g. The t-butoxycarbonyl group, with an aminoacid of general formula IV, followed by the replacement by known methods, of the protecting group Y by a hydrogen atom.

According to a further feature of the present invention the tripeptides of general formula II are obtained by reacting an acid of general formula VII, or an activated derivative thereof, with a tripeptide of the general formula:

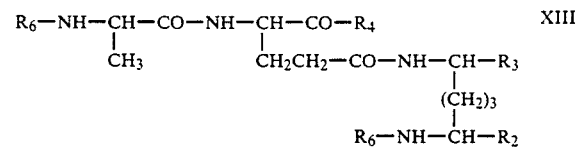

wherein $R_2$, $R_3$ and $R_4$ are as hereinbefore defined and the symbols $R_6$, which may be the same or different, represent a hydrogen atom or a radical $R_5$ as hereinbefore defined, at least one of the symbols $R_6$ representing a hydrogen atom, under the conditions described above for the reaction of an acid of general formula VII with a dipeptide of general formula VIII, followed, when one of the radicals $R_6$ represents an amino-protecting group by conversion, by known methods, of the amino-protecting group into a hydrogen atom, optionally followed, when the radical $R_4$ represents an alkoxy radical containing 1 to 4 carbon atoms which is optionally substituted by a phenyl or nitrophenyl radical, by conversion, by known methods, of the alkoxy radical into a hydroxy group, optionally followed, when one or both of the radicals $R_2$ and $R_3$ represent an alkoxycarbonyl radical in which the alkyl moiety contains 1 to 4 carbon atoms and is optionally substituted by a phenyl or nitrophenyl radical, by conversion, by known methods, of the alkoxycarbonyl radical into a carboxy radical.

The present invention also provides a process for the preparation of the tripeptides of general formula II by means of the Merrifield peptide synthesis in the solid phase.

This process comprises fixing, to a suitable support, an aminoacid of the general formula:

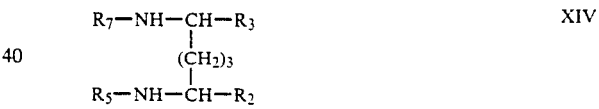

wherein one of the symbols $R_2$ and $R_3$ represents a carboxy radical and the other represents a hydrogen atom, a carbamoyl radical or an alkoxycarbonyl radical in which the alkyl moiety contains 1 to 4 carbon atoms (and is optionally substituted by a phenyl or nitrophenyl radical), $R_5$ represents a fatty acid residue or an amino-protecting group and $R_7$ represents an amino-protecting group, it being understood that if $R_5$ and $R_7$ each represent an amino-protecting group, these protecting groups are different, and, after unblocking the amine group protected by the group $R_7$, reacting with the aminoacid fixed to the support:

(i) a D-glutamic acid derivative in which the amine α-carboxyl groups are suitably protected, i.e. a compound of the general formula:

wherein $R_4$ and $R_7$ are as hereinbefore defined and, after unblocking the amine group protected by the radical $R_7$, reacting the product obtained in either:

(a) a L-alanine derivative of the general formula:

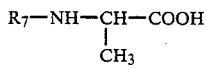
   XVI (wherein R₇ is as hereinbefore defined) and, after unblocking the amine group protected by R₇, optionally reacting the product obtained with a fatty acid of general formula VII to convert the amine group to a group R''—NH— in which R'' represents a fatty acid residue as hereinbefore defined, or (b) a L-alanine derivative of the general formula:

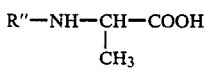
   XVII (wherein R'' is as hereinbefore defined) or (ii) a dipeptide of the general formula:

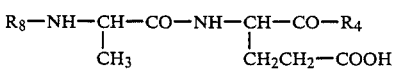
   XVIII wherein R₄ is as hereinbefore defined and R₈ represents a fatty acid residue or an amino-protecting group, it being understood that if R₈ represents an amino-protecting group, the said protecting group is different from the protecting group R₅ of the product of general formula XIV, and, in this case, after unblocking the amine group protected by R₈, optionally reacting the product obtained with an acid of general formula VII, wherein R'—C— is as hereinbefore defined, to convert the amine group to a group R''—NH—, wherein R'' is as hereinbefore defined, and then separating the resulting product from its support and, if necessary, removing the protecting groups from the amine and carboxy groups.

A variant of this process comprises fixing, to a suitable support, a dipeptide of the general formula:

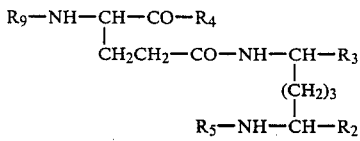
   XIX wherein one of the symbols R₂ and R₃ represents a carboxy radical and the other represents a carbamoyl radical or an alkoxycarbonyl radical in which the alkyl moiety contains 1 to 4 carbon atoms (and is optionally substituted by a phenyl or nitrophenyl radical) and R₄ and R₅ are as hereinbefore defined and R₉ represents an amino-protecting group, it being understood that if R₅ an R₉ each represent an amino-protecting group, these protecting groups are different, and, after unblocking the amine group protected by R₉, reacting with the dipeptide fixed to the support either a L-alanine derivative of general formula XVI, and, after unblocking the amine group protected by R₇, optionally reacting the product obtained with a fatty acid of general formula VII to convert the amine group to a group R''—NH— in which R'' is as hereinbefore defined, or a L-alanine derivative of general formula XVII, and then separating the resulting product from its support and, if necessary, removing the protecting groups from the amine and carboxyl groups.

Another variant of this process comprises fixing to a suitable support, a tripeptide of the general formula:

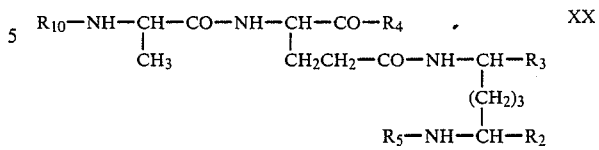
   XX wherein one of the symbols R₂ and R₃ represents a carboxy radical and the other represents a carbamoyl radical or an alkoxycarbonyl radical in which the alkyl moiety contains 1 to 4 carbon atoms (which is optionally substituted by a phenyl or nitrophenyl radical) and R₄ and R₅ are as hereinbefore defined and R₁₀ represents an amino-protecting group, it being understood that if R₅ and R₁₀ each represent an amino-protecting group, these protecting groups are different, and, after unblocking the amine group protected by R₁₀, reacting the product obtained with a fatty acid of general formula VII to convert the amine group to a group $R_{41}$—NH— in which R'' is as hereinbefore defined and separating the resulting product from its support and, if necessary, removing the protecting groups from the amine and carboxy groups.

Particularly suitable supports are chloromethylated or hydroxymethylated styrene/divinylbenzene copolymers. Preferably, a chloromethylated styrene/divinylbenzene copolymer (98/2 to 99/1) is used.

The aminoacid of general formula XIV, the dipeptide of general formula XIX or the tripeptide of general formula XX is fixed to the support by known methods. When a chloromethylated support is used the reaction with the support is generally effected by reacting with aminoacid, the dipeptide or the tripeptide in solution in an organic solvent, e.g. ethanol, and in the presence of an acid acceptor, e.g. triethylamine. It is particularly advantageous to heat the reaction mixture to a temperature close to the boiling point of the solvent.

In the processes described above, the reaction of the aminoacids, peptides or acids of formula VII with an aminoacid fixed to a suitable support is carried out by known methods employed in peptide chemistry. The blocking of groups which must not participate in the reactions, and, where appropriate, the unblocking of the said groups are also carried out by known methods.

The amino-protecting groups of the aminoacid of general formula XIV, of the dipeptide of general formula XIX or of the tripeptide of general formula XX must be chosen so that their removal may be carried out without affecting the aminoacid-support bond. In particular, the radicals R₇, R₈, R₉ and R₁₀ must be different from the radical R₅ if the latter represents an amino-protecting group, and must be such that their removal may be carried out without affecting the protecting group R₅ and without affecting the peptide-support bond.

In general, if the radicals R₂, R₃ or R₄ represent ester groups, they are chosen so that, during the breaking of the peptide-support bond, they can either be retained or be converted into carboxy or carbamoyl radicals, depending on whether the peptide-support bond is broken by acid hydrolysis, alcoholysis or ammonolysis.

The peptide-support bond, which is generally of the benzyl type, is generally broken by treatment with a hydrobromic acid/trifluoroacetic acid mixture.

If necessary, the tripeptides of general formula II can be purified by physical methods (e.g. crystallisation or chromatography) or chemical methods (e.g. The formation of a salt, crystallisation of the salt and then decomposition).

The products according to the invention can be converted by known methods into addition salts with acids or into metal salts or into addition salts with organic bases, depending on the nature of the substituents.

The addition salts with acids can be obtained by reacting the compounds of general formula II with an acid in a suitable solvent. In general, the product is solubilised in water by adding the theoretical amount of acid and the resulting solution is then lyophilised.

The metal salts of the addition salts with organic bases can be obtained by reacting the compounds of general formula II with a base in a suitable solvent. In general, the product is solubilised in water by adding the theoretical amount of base and the resulting solution is then lyophilised.

Preferably the salts of compounds of general formula II are non-toxic salts, i.e. salts the cations, or in the case of acid addition salts, the anions, of which are relatively innocuous to the animal organism in therapeutic doses of the salts so that the beneficial physiological properties inherent in the compounds of general formula II are not vitiated by side effects ascribable to the cations or anions.

Suitable acid addition salts are, for example, the hydrochlorides, sulphates, nitrates, phosphates, acetates, propionates, succinates, benzoates, fumarates, maleates, theophylline-acetates, salicylates, phenolphthalinates and methylene-bis-β-hydroxy-naphthoates.

The new compounds according to the present invention are useful as vaccine adjuvants and immunostimulants; they increase hypersensitivity reactions and/or the production of circulating antibodies against antigens with which they are administered, and they stimulate, in a non-specific manner, defence reactions against certain infections (e.g. The infection caused in mice by the intracellular bacterium *Listeria monocytogenes*).

In vitro, the compounds of general formula II are active at molar concentrates which are generally from $10^{-3}$ to $10^{-8}$, in particular in the following tests:

stimulating the synthesis of DNA (mitogenetic power), in accordance with the technique of G. Marchal, Ann. Immunol. (Inst. Pasteur), 125 C, 519 (1974), stimulating the allogenic reaction (histo- incompatibility reaction) in accordance with the technique of R. W. Dutton, J. exp. Med., 122, 759 (1966), and A. B. Peck and F. H. Bach, J. Immunol. Methods, 3, 147 (1973), stimulating the production of antibodies, in accordance with the technique of P. H. Klesius, Proc. Soc. exp. Biol. Med. (N.Y.), 135, 155 (1970), and H. van Dijk and N. Bloksma, J. Immunol. Methods, 14, 325 (1977), increasing the number of phagocytic macrophages, in accordance with the technique of J. Michl et al., J. exp. Med., 144, 1,465 (1976), and stimulating the acid phosphates and N-acetyl-glucosamidinase activity (lysosome enzymes of macrophages) in the absence of an increase in the lactate dehydrogenase, in accordance with the technique of P. Davies et al., J. exp. Med., 139, 1,262 (1974).

In vivo, in mice, at doses of between 1 and 30 mg/kg, they increase the delayed hypersensitivity and the production of antibodies, in particular in accordance with the technique of T. E. Miller et al., J. Nath. Cancer Inst., 51, 1,669 (1973).

In guinea-pigs, they increase the hypersensitivity reaction and the production of antibodies against bovine gamma-globulin coupled with the hapten dinitrophenol, in accordance with the technique of F. Floc'h'h et al., Immunol. Communic., 7, 41 (1978).

In mice, they stimulate the defense reactions against the infection caused in mice by Listeria monocytogenes, at doses of between 1 and 100 mg/kg, in accordance with the technique of R. M. Fauve and B. Hevin, C. R. Acad, Sci. (D), 285, 1,589 (1977).

In mice, they stimulate the ability of the reticuloendothelial system to take up colloidal carbon, in accordance with the technique of B. N. Halpern et al., Ann. Institut Pasteur, 80,582 (1951).

In rabbits, at doses which are generally between 0.1 and 3 mg/kg, they stimulate the formation of serum antibodies against influenza virus, in accordance with the technique of G. H. Werner et al., Biomedicine, 22, 440 (1975).

Of very particular value are the tripeptides of general formula II wherein $R_1$ represents a hydroxy or alkoxy radical containing 1 to 4 carbon atoms, $R_2$ represents a hydrogen atom or a carbamoyl radical, $R_3$ represents a carboxy radical or an alkoxycarbonyl radical in which the alkyl moiety contains 1 to 4 carbon atoms, the symbol R bonded to the L-alanyl residue is an alkanoyl radical containing 8 to 16 carbon atoms and the symbol R bonded to the amino group in the α-position to the radical $R_2$ is a hydrogen atom. Of more particular value are the products of general formula II in which $R_1$ represents a hydroxy radical, $R_2$ represents a carbamoyl radical, $R_3$ represents a carboxy radical and the symbols R are as just defined above.

The following Examples illustrate the invention.

The new products of general formula II can form complexes with alkali metals or alkaline earth metals. Consequently, the results of elementary analysis can deviate substantially from the theoretical values. However, the products are identified by their aminoacid content, by the C/N ratio and by their homogeneity in thin layer chromatography on silica gel.

EXAMPLE I

Isobutyl chloroformate (1.88 cc) is added to a solution, kept at 10° C., of benzyl N-lauroyl-L-alanyl-α-D-glutamate (7.03 g) in a mixture of dioxan (280 cc) and triethylamine (2.0 cc). The mixture is stirred for 20 minutes at 10° C. and a solution of N-ε-benzyloxycarbonyl-L-lysine (4.04 g) in a mixture of dioxan (30 cc) and 1N sodium hydroxide solution (14.4 cc) is then added. The reaction mixture is stirred for 20 hours at about 18° C. The insoluble material formed is dissolved by adding water (280 cc). The resulting solution is stirred for a further 1 hour and then acidified to pH 3 by adding 1N hydrochloric acid (20 cc). The insoluble material formed is filtered off, washed with water ((20 cc) and dried under reduced pressure (0.3 mm Hg) at 20° C. to yield a white solid (7.72 g) which is chromatographed on a column of diameter 3.5 cm, containing neutral silica gel (230 g). Elution is carried out successively with a mixture of acetone and cyclohexane (9/1 by volume; 700 cc), acetone (1.1 liters) and methanol (1.7 liters), 100 cc fractions being collected. Fractions 22 to 35 are combined and concentrated to dryness under reduced pressure (20 mm Hg) at 45° C. to yield N-α-[0¹-benzyl-N-(N-lauroyl-L-alanyl)-γ-D-glutamyl]-N-ε-benzyloxycarbonyl-L-lysine (5.97 g).

Rf=0.84 [silica gel; n-butanol/pyridine/acetic acid/water (50/20/6/24 by volume)].

N-α-[O¹-Benzyl-N-(N-lauroyl-L-alanyl)-γ-D-glutamyl]-N-ε-benzyloxycarbonyl-L-lysine (1.77 g) is dissolved in methanol (177 cc). Palladium-on-charcoal (containing 3% w/w of palladium; 1.77 g) is added and a slow stream of hydrogen is then passed through the mixture for 4 hours. After filtering and concentrating the filtrate to dryness, the residual oil is taken up in acetone (20 cc). The solution obtained yields a white solid (1.06 g) which is recrystallised from a mixture of ethanol (12 cc) and acetone (24 cc) to yield N-α-[N-(N-lauroyl-L-alanyl-γ-D-glutamyl]-L-lysine (0.9 g) which melts at 180°–186° C. (to give a paste).

Rf=0.29 [silica gel; n-butanol/pyridine/acetic acid/water (50/20/6/24 by volume)].

| Analysis | | | |
|---|---|---|---|
| calculated | C 59.07% | H 9.15% | N 10.60% |
| found | 58.4% | 8.8% | 10.0% |

After total hydrolysis, analysis on a Technicon autoanalyser shows the presence of the following aminoacids:
Ala: 1.02 (theory=1)
Glu: 1.00 (theory=1)
Lys: 0.89 (theory=1)

Benzyl N-lauroyl-L-alanyl-α-D-glutamate can be prepared in accordance with one of the following two methods:

(a) Lauroyl chloride (8 g) dissolved in diethyl ether (75 cc) is added, in the course of 37 minutes, to a solution of benzyl L-alanyl-α-D-glutamate hydrochloride (12.75 g) in 1N sodium hydroxide solution (75 cc), and 1N sodium hydroxide solution (37.4 cc) is added simultaneously to keep the pH of the reaction mixture between 8 and 9. The mixture is stirred for 1 hour 20 minutes. After decantation, the aqueous phase is acidified to pH 2 by adding 1N hydrochloric acid (60 cc) and extracted 3 times with ethyl acetate (300 cc in total). The combined organic extracts are washed with water (25 cc), dried over anhydrous sodium sulphate and concentrated to dryness under reduced pressure (20 mm Hg) at 45° C. to yield a white solid (7.4 g) which is chromatographed on neutral silica gel (80 g) contained in a column of diameter 2 cm. Elution is carried out successively with a mixture of ethyl acetate and methanol (8/2 by volume; 100 cc) and a mixture of ethyl acetate and methanol (1/1 by volume; 200 cc), 50 cc fractions being collected. Fraction 1 is concentrated to dryness under reduced pressure (20 mm Hg) at 45° C. to yield benzyl N-lauroyl-L-alanyl-α-D-glutamate (2 g) which melts at 130° C. Fractions 2 to 4 are likewise concentrated to dryness and chromatographed on neutral silica gel (0.063–0.20 mm; 100 g) contained in a column of diameter 2 cm. Elution is carried out with acetone (250 cc), 25 cc fractions being collected. Fractions 1 and 2 are concentrated to dryness under reduced pressure (20 mm Hg) at 45° C. to yield benzyl N-lauroyl-L-alanyl-α-D-glutamate (4.07 g) which melts at 130° C. and has the following characteristics:

Rf=0.9 [silica gel; n-butanol/pyridine/acetic acid/water (50/20/6/24 by volume)].

| analysis | | | |
|---|---|---|---|
| calculated | C 66.10% | H 8.63% | N 5.71% |
| found | 66.3% | 8.8% | 5.6% |

(b) Isobutyl chloroformate (31 cc) is added to a solution, kept at a temperature of the order of 10° C., of lauric acid (47.75 g) in dioxan (3 liters) and triethylamine (33.3 cc). The mixture is stirred for 20 minutes at 10° C. and a solution, cooled to 10° C., of benzyl L-alanyl-α-D-glutamate hydrochloride (88.95 g) in a mixture of dioxan (1 liter), water (476 cc), and 1N sodium hydroxide solution (476 cc) is then added in the course of 10 minutes. The reaction mixture is stirred for 1 hour at 10° C. and then for 18 hours at a temperature of the order of 20° C.; it is then diluted by adding water (4 liters), acidified to pH 2 by adding 1N hydrochloric acid (about 475 cc) and kept for 2 hours at 0° C. The resulting precipitate is filtered off, washed successively with water (500 cc) and diethyl ether (500 cc) and then dried under reduced pressure (20 mm Hg) at 20° C. The product is suspended in diethyl ether (800 cc), the suspension is stirred for 1 hour and the product is filtered off and washed twice with diethyl ether (200 cc in total). After drying under reduced pressure (20 mm Hg) at 20° C., benzyl N-lauroyl-L-alanyl-α-D-glutamate (71.79 g), which melts at 130° C., is obtained.

Rf=0.77 [silica gel; ether acetate/methanol (4/1 by volume)].

Benzyl L-alanyl-α-D-glutamate hydrochloride can be prepared in the following manner:

Benzyl N-t-butoxycarbonyl-L-alanyl-α-D-glutamate (97.16 g) is dissolved in a 1.7N anhydrous solution of hydrogen chloride in acetic acid (970 cc). The resulting solution is stirred for 2 hours, anhydrous diethyl ether (3.8 liters) is then added rapidly and the mixture is left to stand for 2 hours at 0° C. The oily precipitate which has formed is separated from the supernatant liquor by decantation and dissolved in acetone (500 cc); the solution thus obtained is concentrated to dryness under reduced pressure (20 mm Hg) at 50° C. to yield benzyl L-alanyl-α-D-glutamate hydrochloride (88.9 g).

Benzyl N-t-butoxycarbonyl-L-alanyl-α-D-glutamate can be prepared in accordance with the method of E. Bricas et al., Biochemistry 9, 823 (1970).

N-ε-Benzyloxycarbonyl-L-lysine can be prepared in accordance with the method of A. Neuberger et al., Biochem. J., 37, 515 (1943).

EXAMPLE 2

Isobutyl chloroformate (0.65 cc) is added to a solution, kept at −10° C., of benzyl N-lauroyl-L-alanyl-α-D-glutamate (2.45 g) in a mixture of tetrahydrofuran (80 cc) and triethylamine (0.70 cc). The mixture is stirred for 20 minutes at −10° C., and a solution, cooled to −10° C., of benzyl N-ε-benzyloxycarbonyl-L-lysinate hydrochloride (2.24 g) in a mixture of tetrahydrofuran (40 cc) and triethylamine (0.77 cc) is then added. The reaction mixture is stirred for 2 hours at −10° C. and then for 2 days at about 20° C. The reaction mixture is then concentrated to dryness under reduced pressure (20 mm Hg) at 40° C. The resulting white solid is taken up in ethyl acetate (100 cc) at 40° C., triturated to a powder filtered off, triturated again in 0.1N hydrochloric acid (50 cc), filtered off and dried under reduced pressure (0.3 mm Hg). This yields benzyl N-α-[O¹-benzyl-N-(N-lauroyl-L-alanyl)-γ-D-glutamyl]-N-ε-benzyloxycarbonyl-L-lysinate (2.69 g).

Rf=0.80 [silica gel; ethyl acetate/methanol (9/1 by volume)].

Benzyl N-α-[O$^1$-benzyl-N-(N-lauroyl-L-alanyl)-γ-D-glutamyl]-N-ε-benzyloxycarbonyl-L-lysinate (2.65 g) is dissolved in acetic acid (265 cc). Palladium-on-charcoal (containing 3% w/w of palladium; 2.65 g) is added and a slow stream of hydrogen is passed through the mixture for 3 hours. Filtering and concentrating the filtrate to dryness under reduced pressure (20 mm Hg) at 50° C. yields N-α-[N-(N-lauroyl-L-alanyl)-γ-D-glutamyl]-L-lysine (1.81 g) which is identical to the product obtained in Example 1.

Benzyl N-ε-benzyloxycarbonyl-L-lysinate can be prepared in accordance with the method of T. Shiba et al, Bull. Chem. Soc. Japan 33, 1,721 (1960).

EXAMPLE 3

Isobutyl chloroformate (3.17 cc) is added to a solution, kept at about 10° C., of benzyl N-lauroyl-L-alanyl-α-D-glutamate (11.96 g) in a mixture of dioxan (490 cc) and triethylamine (3.43 cc). The solution is stirred for 20 minutes at about 10° C. and a solution of N$^6$-benzyloxycarbonyl-D,D/L,L-2,6-diaminopimelamic acid (8.87 g), of 88.8% purity (perchloric acid determination), in a mixture of water (219 cc) and 1N sodium hydroxide solution (24.4 cc) is then added. The reaction mixture is stirred for 2 hours at a temperature of the order of 10° C. and then for 15 hours at a temperature of the order of 20° C.; it is then filtered. Water (360 cc) is added to the filtrate, and the small amount of insoluble material formed is filtered off. The filtrate is acidified to pH 2 by adding 1N hydrochloric acid (49 cc). The precipitate formed is filtered off, washed 3 times with water (750 cc in total) and dried to yield a white powder (16.3 g) which is chromatographed on neutral silica gel (0.0635–0.20 mm; 800 g) contained in a column of diameter 6 cm. To carry out the chromatography, the powder (16.3 g) is dissolved in methanol (800 cc), and Fontainebleau sand (160 g) is added to the resulting solution. The mixture is evaporated to dryness under reduced pressure (20 mm Hg) at 60° C. and the residue thus obtained is introduced onto the silica column. Elution is carried out successively with ethyl acetate (1 liter), a mixture of ethyl acetate and methanol (9/1 by volume; 4 liters), a mixture of ethyl acetate and methanol (85/15 by volume; 7 liters) and a mixture of ethyl acetate and methanol (1/1 by volume; 4 liters), 250 cc fractions being collected. Fractions 45 to 60 are combined and concentrated to dryness under reduced pressure (20 mm Hg) at 60° C. to yield N$^2$-[O$^1$-benzyl-N-(N-lauroyl-L-alanyl)-γ-D-glutamyl]-N$^6$-benzyloxycarbonyl-D,D/L,L-2,6-diaminopimelamic acid 9.4 g).

Rf=0.83 [silica gel; n-butanol/pyridine/acetic acid/water (50/20/6/24 by volume)].

N$^2$-[O$^1$-Benzyl-N-(N-lauroyl-L-alanyl)-γ-D-glutamyl]-N$^6$-benzyloxycarbonyl-D,D/L,L-2,6-diaminopimelamic acid (4.07 g) is dissolved in acetic acid (200 cc). Palladium-on-charcoal (containing 3% w/w of palladium; 4 g) is added and a slow stream of hydrogen is passed through the mixture for 7 hours. After filtering and concentrating the filtrate to dryness under reduced pressure (20 mm Hg) at 60° C., the resulting hard foam is taken up 3 t times in methylcyclohexane (45 cc in total) and the mixture is evaporated to dryness each time under reduced pressure (20 mm Hg) at 60° C. The powder thus obtained is dried under reduced pressure (0.3 mm Hg) at 50° C. to yield N$^2$-(N-lauroyl-L-alanyl-γ-D-glutamyl)-D,D/L, L-2,6-diaminopimelamic acid (2.76 g).

Rf=0.49 (silica gel; acetic acid).

| Analysis: | | | |
|---|---|---|---|
| calculated = | C 56.72% | H 8.64% | N 12.25% |
| found = | 53.4% | 8.5% | 10.9% |

After total hydrolysis, analysis on a Technicon autoanalyser shows the presence of the following aminoacids:
Ala 1.00 (theory=1)
Dap 0.99 (theory=1)
Glu 1.05 (theory=1)

N$^6$-Benzyloxycarbonyl-D,D/L,L-2,6-diaminopimelamic acid can be prepared in the following manner:

Cupric bromide (4.35 g) dissolved in water (44 cc) is added to a solution of D,D/L,L-2,6diaminopimelamic acid diydrochloride (9.7 g) in water (63 cc), and the solution adjusted to pH 10 by adding 1N sodium hydroxide solution (37 cc). The reaction mixture is stirred for 2 hours at about 20° C. A small amount of insoluble material is filtered off and the filtrate is then cooled to a temperature between −3° C. and 0° C. Sodium bicarbonate (9.2 g) is added and benzyl chloroformate (7.9 cc) is then added dropwise in the course of 30 minutes. The reaction mixture is stirred for 18 hours at a temperature of the order of 20° C. The blue precipitate formed is filtered off and washed with water (15 cc), twice with ethanol (30 cc in total) and with diethyl ether (15 cc). Drying under reduced pressure (20 mm Hg) at 50° C. yields the copper complex of N$^6$-benzyloxycarbonyl-D,D/L,L-2,6-diaminopimelamic acid (9.6 g) which is added to 1N hydrochloric acid (60 cc). The mixture is stirred for 1 hour at a temperature of the order of 20° C. An insoluble material is filtered off. Methanol (30 cc) is added to the filtrate and a stream of hydrogen sulphide is passed through the mixture for 1½ hours. The mixture is left to stand for 16 hours. The resulting black slurry is filtered and the solid is washed 4 times with water (160 cc in total). The combined filtrates are concentrated to a volume of 30 cc under reduced pressure (20 mm Hg) at 50° C., adjusted to pH 9 by adding triethylamine (7.5 cc), diluted by adding water (20 cc) and adjusted to pH 6 by adding 1N hydrochloric acid (5.5 cc). The white slurry thus obtained is kept at 0° C. for 2 hours. The product is filtered off, washed successively with water (20 cc) and ethanol (20 cc) and dried under reduced pressure to yield N$^6$-benzyloxycarabonyl-D,D,L,L,-2,6-diaminopimelamic acid (5.8 g) of 96% purity (perchloric acid determination).

D,D/L,L-2,6-Diaminopimelamic acid dihydrochloride can be prepared in the following manner:

D,D/L,L-2,6-Dibenzyloxycarbonylaminopimelamic acid (83 g) is dissolved in a mixture of methanol (1.6 liters) and concentrated hydrochloric acid (d=1.19; 14.6 cc). Palladium-on-charcoal (containing 3% w/w of palladium; 83 g) is added and a stream of hydrogen is passed through the mixture for 10 hours. After filtering and concentrating the filtrate to dryness under reduced pressure (20 mm Hg) at 60° C., D,D/L,L-2,6-diaminopimilamic acid dihydrochloride (40.5 g) is obtained in the form of a hard foam.

D,D/L,L-2,6-Dibenzyloxycarbonylaminopimelamic acid can be prepared in the following manner:

The monobenzyl ester of D,D/L,L-2,6-dibenzyloxycarbonylaminopimelic acid (168 g) is dissolved in methanol (1.68 liters). The solution is cooled to about 0° C. and saturated with ammonia. As soon as it is saturated, it is transferred into three 1 liter autoclaves. After these autoclaves have been closed, they are kept for 40 hours at about 20° C. After degassing, the solution thus obtained is concentrated under reduced pressure (20 mm Hg) at 60° C. The residue is dissolved in water (2 liters) and the resulting solution is adjusted to pH 2 by adding 4N hydrochloric acid. A gummy precipitate is formed and this is isolated by decantation, triturated with diethyl ether (2 liters), filtered off and washed twice with diethyl ether (400 cc in total) and twice with water (400 cc in total). After drying, D,D/L,L,-2,6-dibenzyloxycarbonylaminopimelamic acid (83.5 g) which melts at 145°–150° C., is obtained.

Rf=0.69 [silica gel; n-butanol/ethanol/water/concentrated ammonia (4/4/1/1 by volume)].

The monobenzyl ester of D,D/L,L-2,6-dibenzyloxycarbonylaminopimelic acid can be prepared in accordance with the method of A Arendt et al., Roczniki Chemii Ann. Soc. Chim. Polonorum 48, 1,305 (1974) [Chem. Abstr., 82, 31497 g (1975)].

EXAMPLE 4

Isobutyl chloroformate (0.81 cc) is added to a solution, kept at −5° C., of N-lauroyl-L-alanyl-D-isoglutamine (2.5 g) in dimethylformamide (150 cc) and triethylamine (0.87 cc). The mixture is stirred for 20 minutes at −5° C. and a solution, cooled to +2° C., of $N^6$-benzyloxycarbonyl-D,D/L,L-2,6-diaminopimelamic acid (2.02 g) in a mixture of water (62.5 cc) and 1N sodium hydroxide solution (6.25 cc) is then added. The reaction mixture is stirred for 1 hour at 0° C. and then for 18 hours at about 20° C. and is subsequently filtered. The filtrate, diluted by adding water (300 cc) is acidified to pH 1 by adding 1N hydrochloric acid (15 cc). The precipitate which has appeared is filtered off, washed 3 times with water (30 cc in total) and then dried to yield a white solid (2.03 g) to which a product (680 mg) obtained under similar conditions is added. The mixture is dissolved in acetic acid (30 cc) containing neutral silica gel (0.04–0.063 mm; 5 g). The mixture is concentrated to dryness and the residue is then deposited on a column of diameter 2 cm, containing neutral silica gel (0.04–0.063 mm; 60 g). Elution is carried out successively with a mixture of ethyl acetate and acetic acid (9/1 by volume; 400 cc), a mixture of ethyl acetate and acetic acid (8/2 by volume; 360 cc), a mixture of ethyl acetate and acetic acid (7/3 by volume; 240 cc), a mixture of ethyl acetate and acetic acid (1/1 by volume; 160 cc) and acetic acid (480 cc), 40 cc fractions being collected. Fractions 17 to 49 are combined and concentrated to dryness to yield $N^2$-[N-(N-lauroyl-L-alanyl)-D-isoglutaminyl]-$N^6$-benzyloxycarbonyl-D,D/L,L-2,6-diaminopimelamic acid (1.78 g).

Rf=0.65 [silica gel; ethyl acetate/acetic acid (3/1 by volume)].

$N^2$-[N-(N-Lauroyl-L-alanyl)-D-isoglutaminyl]-$N^6$-benzyloxycarbonyl-D,D/L,L-2,6-diaminopimelamic acid (1.76 g) is dissolved in acetic acid (80 cc). Palladium-on-charcoal (containing 3% w/w of palladium; 1.76 g) is added and a stream of hydrogen is then passed through the mixture for 2½ hours. After filtration, the filtrate is concentrated to about 5 cc and diluted by adding diethyl ether (100 cc). The precipitate formed is filtered off, washed twice with diethyl ether (40 cc in total) and dried to yield $N^2$-[N-(N-lauroyl-L-alanyl)-D-isoglutaminyl]-D,D/L,L-2,6-diaminopimelamic acid (1.37 g).

Rf=0.40 [silica gel; n-butanol/pyridine/acetic acid/water (50/20/6/24 by volume)].

N-Lauroyl-L-alanyl-D-isoglutamine can be prepared in the following manner:

Benzyl N-lauroyl-L-alanyl-D-isoglutaminate (6.6 g) is dissolved in acetic acid (330 cc). Palladium on charcoal (containing 3% w/w of palladium; 6.6 g) is added and a slow stream of hydrogen is then passed through the mixture for 2 hours. After filtering the reaction mixture, the filtrate is poured into water (3 liters). After standing for 2 hours at 0° C., the precipitate which has appeared is filtered off, washed twice with water (80 cc in total) and then dried to yield a product (5.16 g) to which a product (0.5 g) obtained under similar conditions is added. The mixture is dissolved in boiling methanol (90 cc), and water (45 cc) is added to the resulting solution. After standing for 2 hours at a temperature of the order of 20° C., the crystals which have appeared are filtered off, washed twice with water (60 cc in total) and dried under reduced pressure (20 mm Hg) to yield N-lauroyl-L-alanyl-D-isoglutamine (5.1 g) which melts at 163° C.

Rf=0.18 [silica gel; ethyl acetate/methanol (4/1 by volume)].

| Analysis: | | | |
|---|---|---|---|
| calculated = | C 60.12% | H 9.33% | N 10.52% |
| found = | 60.2% | 9.5% | 10.9% |

Benzyl N-lauroyl-L-alanyl-D-isoglutaminate can be prepared in the following manner:

Isobutyl chloroformate (2.54 cc) is added to a solution, kept at 0° C., of lauric acid (3.9 g) in anhydrous toluene (156 cc) and triethylamine (2.7 cc). The mixture is stirred for 20 minutes at 0° C. and a solution, cooled to 0° C., of benzyl L-alanyl-D-isoglutaminate hydrochloride (6.7 g) in water (52 cc) and triethylamine (2.7 cc) is then added. The reaction mixture is stirred for 65 hours at a temperature of the order of 20° C. to yield a reaction mixture of gelatinous appearance, to which ethyl acetate (150 cc) is added. The precipitate is filtered off, washed with water (30 cc) and then dried to yield: benzyl N-lauroyl-L-alanyl-D-isoglutaminate (7.6 g) in the form of a white powder. The aqueous phase of the above filtrate is extracted twice with ethyl acetate (100 cc in total), the ethyl acetate phase is combined with the organic phase of the filtrate and the combined phase is washed with 0.1N hydrochloric acid (125 cc) and water (120 cc), dried over magnesium sulphate and then concentrated to dryness under reduced pressure (20 mm Hg) at 50° C. to yield a further 1.5 g of benzyl N-lauroyl-L-alanyl-D-isoglutaminate. The product (7.6 g and 1.5 g) is recrystallised from methanol (120 cc) to yield benzyl N-lauroyl-L-alanyl-D-isoglutaminate (6.6 g) which melts at 169° C.

Rf=0.13 [silica gel; ethyl acetate].

Benzyl L-alanyl-D-isoglutaminate hydrochloride can be prepared in accordance with the method of S. Kusumoto, Bull. Chem. Soc. Japan 49, 533 (1976).

EXAMPLE 5

Isobutyl chloroformate (0.91 cc) is added to a solution, kept at 0° C., of benzyl N-octanoyl-L-alanyl-α-D-glutamate (3.04 g) in tetrahydrofuran (150 cc) and triethylamine (0.98 cc). The mixture is stirred for 20 minutes at 0° C. and a solution, cooled to 2° C., of $N^6$-benzyloxcarbonyl-D,D/L,L-2,6-diaminopimelamic acid (2.26 g) in a mixture of water (70 cc) and 1N sodium hydroxide solution (7 cc) is then added. The reaction mixture is stirred for 1 hour at 0° C. and then for 20 hours at a temperature of the order of 20° C. The tetrahydrofuran is then evaporated off under reduced pressure (20 mm Hg) at 50' C. The concentrate is diluted by adding water (50 cc) and acidified to pH 1 by adding 1N hydrochloric acid (10 cc). The resulting white precipitate if filtered off, washed 3 times with water (75 cc in total) and then dried to yield a white solid (4.73 g) which is chromatographed on a column of diameter 2.2 cm, containing neutral silica gel (0.04–0.063 mm; 100 g). To carry out the chromatography, the product is dissolved in acetic acid (20 cc). Neutral silica gel 10 g) is added to the resulting solution, and the mixture is concentrated to dryness under reduced pressure (20 mm Hg) at 50° C. The residue thus obtained is introduced onto the column and elution is carried out successively with ethyl acetate (280 cc), a mixture of ethyl acetate and acetic acid (9/1 by volume; 360 cc), a mixture of ethyl acetate and acetic acid (8/2 by volume; 200 cc) and a mixture of ethyl acetate and acetic acid (1/1 by volume; 160 cc), 40 cc fractions being collected. Fractions 13 to 23 are combined and concentrated to dryness under reduced pressure (20 mm Hg) at 50°C. to yield an oil which solidifies in diethyl ether. After filtering off and drying the solid, $N^2$-[$O^1$-benzyl-N-(N-octanoyl-L-alanyl)-γ-D-glutamyl]-$N^6$-benzyloxycarbonyl-D,D/L,L- 2,6-diaminopimelamic acid (2.84 g) is obtained.

Rf=0.68 [silica gel; ethyl acetate/acetic acid (3/1 by volume)].

$N^2$-[$O^1$-Benzyl-N-(N-octanoyl-L-alanyl)-γ-D-glutamyl]-$N^6$-benzyloxycarbonyl-D,D/L,L-2,6-diaminopimelamic acid (2.82 g) is dissolved in acetic acid (80 cc). Palladium-on-charcoal (containing 3% w/w of palladium; 2.82 g) is added and a stream of hydrogen is then passed through the mixture for 2½ hours. After filtration, the filtrate is concentrated to about 5 cc under reduced pressure (20 mm Hg) at 50° C. and diluted by adding diethyl ether (100 cc) to yield a precipitate which is filtered off, washed with diethyl ether (20 cc) and then dried. This yields $N^2$-[N-(N-octanoyl-L-alanyl)-γ-D-glutamyl]-D,D/L,L-2,6-diaminopimelamic acid (2.0 g) which melts at 160°-164° C. (to give a paste).

Rf=0.30 [silica gel; n-butanol/pyridine/acetic acid/water (50/20/6/24 by volume)].

| Analysis: | | | |
|---|---|---|---|
| calculated = | C 53.58% | H 8.02% | N 13.58% |
| found = | 53.05% | 8.17% | 13.06% |

After total hydrolysis, analysis on a Technicon autoanalyser shows the presence of the following aminoacids:
Ala 1.00 (theory=1)
Dap 0.95 (theory=1)
Glu 1.02 (theory=1)

Benzyl N-octanoyl-L-alanyl-α-D-glutamate can be prepared in the following manner:

Isobutyl chloroformate (3.6 cc) is added to a solution, kept at −1° C., of octanoic acid (3.95 g) in tetrahydrofuran (140 cc) and triethylamine (3.8 cc). The mixture is stirred for 20 minutes at −1° C. and a solution, cooled to 0° C., of benzyl L-alanyl-α-D-glutamate hydrochloride (9.45 g) in a mixture of 1N sodium hydroxide solution (54.8 cc) and water (30 cc) is then added. The reaction mixture is stirred for 1 hour at −1° C. and then for 20 hours at about 20° C. It is then acidified to pH 1 by adding 1N hydrochloric acid. The tetrahydrofuran is evaporated off under reduced pressure (20 mm Hg) at 45° C. and the concentrate is then extracted with ethyl acetate (100 cc). The organic phase thus obtained is washed twice with 1N hydrochloric acid (50 cc in total) and with a saturated solution of sodium chloride (25 cc) and concentrated to dryness under reduced pressure (20 mm Hg) at 45° C. to yield a pale yellow oil (10 g) which is chromatographed on a column of diameter 2.5 cm, containing neutral silica gel (0.63–0.20 mm; 200 g). Elution is carried out with ethyl acetate, 100 cc fractions being collected. Fractions 7 to 9 are combined and concentrated to dryness under reduced pressure (20 mm Hg) at 45° C. The resulting residue is triturated in a mixture of diethyl ether and petroleum ether (b.p.=35°-60° C.) (¼ by volume; 100 cc), filtered off and dried. Benzyl N-octanoyl-L-alanyl-α-D-glutamate (3.27 g) is thus obtained in the form of a white powder.

Rf=0.56 [silica gel; ethyl acetate/methanol (8/2 by volume].

EXAMPLE 6

Isobutyl chloroformate (0.70 cc) is added to a solution, kept at 2° C., of benzyl N-palmitoyl-L-alanyl-α-D-glutamate (2.91 g) in tetrahydrofuran (120 cc) and triethylamine (0.75 cc). The mixture is stirred for 20 minutes at 2° C. and a solution, cooled to 2° C., of $N^6$-benzyloxycarbonyl-D,D/L,L-2,6-diaminopimelamic acid (1.726 g) in a mixture of water (53.4 cc) and 1N sodium hydroxide solution (5.34 cc) is then added. The reaction mixture is stirred for 1 hour at 2° C. and then for 18 hours at a temperature of the order of 20° C. The tetrahydrofuran is evaporated off under reduced pressure (20 mm Hg) at 50° C. The concentrate is diluted by adding water (50 cc) and acidified to pH 1 by adding 1N hydrochloric acid (10 cc). The resulting white precipitate is filtered off, washed 3 times with water (75 cc in total) and dried to yield a white solid (4.15 g) which is chromatographed on a column of diameter 3 cm, containing neutral silica gel (0.04–0.063 mm; 85 g). To carry out the chromatography, the product is dissolved in acetic acid at 60° C. Neutral silica gel (10 g) is added to the resulting solution and the mixture is concentrated to dryness under reduced pressure (20 mm Hg) at 50° C. The residue thus obtained is introduced onto the column and elution is carried out successively with ethyl acetate (320 cc), a mixture of ethyl acetate and acetic acid (9/1 by volume; 360 cc) and a mixture of ethyl acetate and acetic acid (8/2 by volume; 320 cc), 40 cc fractions being collected. Fractions 14 to 22 are combined and concentrated to dryness under reduced pressure (20 mm Hg) at 50° C.

The resulting residue is triturated in diethyl ether (50 cc), filtered off and dried. $N^2$[$O^1$-Benzyl-N-(N-palmitoyl-L-alanyl-γ-D-glutamyl]-$N^6$-benzyloxycarbonyl-D,D/L,L-2,6-diaminopimelamic acid (2.20 g) is thus obtained.

Rf=0.75 [silica gel; ethyl acetate/acetic acid (3/1 by volume)].

$N^2$-[$O^1$-Benzyl-N-(N-palmitoyl-L-alanyl)-γ-D-glutamyl]-$N^6$-benzyloxycarbonyl-D,D/L,L-2,6-diaminopimelamic acid (2.14 g) is dissolved in acetic acid (80 cc). Palladium-on-charcoal (containing 3% w/w of palladium; 2.14 g) is added and a slow stream of hydrogen is then passed through the mixture for 2½ hours. After filtration, the filtrate is concentrated to about 5 cc under reduced pressure (20 mm Hg) at 50° C. and is then diluted by adding diethyl ether (100 cc) to yield a precipitate which is filtered off, washed twice with diethyl ether (20 cc in total) and dried. $N^2$-[N-(N-Palmitoyl-L-alanyl)-γ-D-glutamyl]-D,D/L,L2,6-diaminopimelamic acid (1.58 g) is thus obtained.

Rf=0.30 [silica gel; n-butanol/pyridine/acetic/acid/-water (50/20/6/24 by volume)].

Benzyl N-palmitoyl-L-alanyl-α-D-glutamate can be prepared in the following manner:

Isobutyl chloroformate (3.6 cc) is added to a solution, kept at 0° C., of palmitic acid (7.03 g) in tetrahydrofuran (140 cc) and triethylamine (3.8 cc). The mixture is stirred for 20 minutes at 0° C. and a solution, cooled to 0° C., of benzyl L-alanyl-α-D-glutamate hydrochloride ((9.45 g) in a mixture of 1N sodium hydroxide solution (54.8 cc) and water (30 cc) is then added. The reaction mixture is stirred for 1 hour at 0° C. and then for 18 hours at about 20° C.; it is then acidified to pH 1 by adding 1N hydrochloric acid (70 cc). The precipitate formed is filtered off, washed 5 times with water (200 cc in total) and dried to yield a white powder (12.11 g) which is chromatographed on a column of diameter 2.5 cm, containing neutral silica gel (0.063–0.20 mm; 200 g). Elution is carried out successively with ethyl acetate (200 cc), a mixture of ethyl acetate and methanol (9/1 by volume; 300 cc), a mixture of ethyl acetate and methanol (8/2 by volume; 1.6 liters) and a mixture of ethyl acetate and methanol (6/4 volume; 400 cc), 100 cc fractions being collected. Fractions 5 to 23 are combined and concentrated to dryness under reduced pressure (20 mm Hg) at 45° C. to yield a solid (5.18 g) which is triturated in boiling diethyl ether (50 cc) for ½ hour. After cooling to a temperature of the order of 20° C., the insoluble material is filtered off, washed 3 times with diethyl ether (75 cc in total) and then dried. Benzyl N-palmitoyl-L-alanyl-α-D-glutamate (2.94 g) is thus obtained.

Rf=0.77 [silica gel; ethyl acetate].

EXAMPLE 7

Isobutyl chloroformate (1.3 cc) is added to a solution, kept at −5° C., of benzyl N-lauroyl-L-alanyl-α-D-glutamate (4.91 g) in a mixture of tetrahydrofuran (250 cc) and triethylamine (1.4 cc). The mixture is stirred for 20 minutes at −5° C. and a solution, cooled to 0° C., of methyl N-ε-benzyloxycarbonyl-L-lysinate hydrochloride (3.32 g) in a mixture of 1N sodium hydroxide solution (10 cc) and water (10 cc) is then added. The reaction mixture is stirred for 10 minutes at about −5° C. and then for 4 days at a temperature of the order of 20° C. The reaction mixture is then acidified to pH 1 by adding 1N hydrochloric acid (20 cc). The tetrahydrofuran is evaporated off under reduced pressure (20 mm Hg) at 45° C. The concentrate obtained is extracted 5 times with chloroform (150 cc in total). The combined chloroform phases are washed with 0.1N hydrochloric acid (40 cc) and dried over sodium sulphate. Concentration to dryness under reduced pressure (20 mm Hg) at 50° C. yields a pale yellow oil which is dissolved in chloroform (60 cc) containing neutral silica gel (0.04–0.063 mm; 15 g). The mixture is concentrated to dryness and then introduced onto a column of diameter 3 cm, containing neutral silica gel (0.04–0.063 mm; 150 g). Elution is carried out successively with ethyl acetate (2.5 liters) and a mixture of ethyl acetate and acetic acid (95/5 by volume; 400 cc), 100 cc fractions being collected. Fractions 6 to 27 are combined and concentrated to dryness under reduced pressure (20 mm Hg) at 50° C. Methyl N-α-[O¹-benzyl-N-(N-lauroyl-L-alanyl)-γ-D-glutamyl]-N-ε-benzyloxycarbonyl-L-lysinate (3.47 g) is thus obtained in the form of a white powder.

Rf=0.70 [silica gel; ethyl acetate/acetic acid (95/5 by volume)].

Rf=0.40 [silica gel; ethyl acetate].

Methyl N-α-[O¹benzyl-N-(n-lauroyl-L-alanyl)-γ-D-glutamyl]-N-ε-benzyloxycarbonyl-L-lysinate (3.43 g) is dissolved in acetic acid (70 cc). Palladium-on-charcoal (containing 3% w/w of palladium; 3.43 g) is added and a slow stream of hydrogen is then passed through the mixture for 2 hours. The catalyst is filtered off and washed twice with acetic acid (20 cc in total) and the combined filtrates are concentrated to dryness under reduced pressure (20 mm Hg) at 50° C. The residue thus obtained is triturated in diethyl ether (50 cc) to yield a powder which is filtered off and dried in air. Methyl N-α-[N-(N-lauroyl-L-alanyl)-γ-D-glutamyl]-L-lysinate (1.89 g) is thus obtained.

Rf=0.50 [silica gel; n-butanol/pyridine/acetic acid/-water (50/20/6/24 by volume)].

Rf=0.29 [silica gel; acetic acid].

EXAMPLE 8

Isobutyl chloroformate (1.6 cc) is added to a solution, kept at −5° C., of benzyl N-lauroyl-L-alanyl-α-D-glutamate (6.07 g) in a mixture of tetrahydrofuran (280 cc) and triethylamine (1.74 cc). The mixture is stirred for 20 minutes at −5° C.; a solution, cooled to 3° C., of $N^6$-benzyloxycarbonyl-meso-2(L),6(D)-diaminopimelamic acid (4 g) in a mixture of 1N sodium hydroxide solution (12.4 cc) and water (124 cc) is then added. The reaction mixture is stirred for 10 minutes at about 0° C. and then for 70 hours at about 20° C. The reaction mixture is then acidified to pH 1 by adding 1N hydrochloric acid (20 cc). The tetrahydrofuran is evaporated off under reduced pressure (20 mm Hg) at 50° C. The concentrate obtained contains a white precipitate which is filtered off, washed 3 times with 0.1N hydrochloric acid (150 cc in total) and 3 times with water (150 cc in total) and dried under reduced pressure (20 mm Hg) at 20° C. to yield a white powder (9.15 g) which is dissolved in acetic acid (100 cc) containing neutral silica gel (0.04–0.063 mm; 20 g). The mixture is concentrated to dryness and then introduced onto a column of diameter 5 cm, containing neutral silica gel (0.04–0.063 mm; 400 g).

Elution is carried out successively with ethyl acetate (1.6 liters), a mixture of ethyl acetate and acetic acid (97.5/2.5 by volume; 900 cc) a mixture of ethyl acetate and acetic acid (95/5 by volume; 1,200 cc), a mixture of ethyl acetate and acetic acid (92.5/7.5 by volume; 900 cc), a mixture of ethyl acetate and acetic acid (90/10 by volume; 900 cc), a mixture of ethyl acetate and acetic acid (85/15 by volume; 300 cc) and a mixture of ethyl acetate and acetic acid (80/20 by volume; 3,200 cc), 100 cc fractions being collected. Fractions 61 to 90 are combined and concentrated to dryness under reduced pressure (20 mm Hg) at 50° C. The resulting white solid is washed twice with diethyl ether (100 cc in total) and dried under reduced pressure (0.3 mm Hg) at 60° C. $N^2$-[O¹-Benzyl-N-(N-lauroyl-L-alanyl)-γ-D-glutamyl-$N^6$-benzyloxycarbonyl-meso-2(L),6(D)-diaminopimelamic acid (6.3 g) is thus obtained.

Rf=0.77 [silica gel; ethyl acetate/acetic acid (3/1 by volume)].

$N^2$-[$O^1$-Benzyl-N-(N-lauroyl-L-alanyl)-γ-D-glutamayl]-$N^6$-benzyloxycarbonyl-meso-2(L),6(D)-diaminopimelamic acid (8.2 g) is dissolved in acetic acid (225 cc). Palladium-on-charcoal (containing 3% w/w of palladium; 8.2 g) is added and a slow stream of hydrogen is passed through the mixture for 3½ hours. After filtering and concentrating the filtrate to dryness under reduced pressure (20 mm Hg) at 50° C., the resulting oil is triturated in diethyl ether (100 cc) until it has all been converted to powder, and the mixture is then filtered and dried under reduced pressure (0.3 mm Hg) at 50° C. to yield a powder (5.9 g). The powder (0.9 g) is dissolved in acetic acid and the solution is filtered over a column of neutral silica gel (0.04–0.063 mm) of diameter 2 cm and height 2 cm. The filtrate is concentrated to dryness under reduced pressure (20 mm Hg) at 50° C. The resulting residue is taken up in diethyl ether (50 cc), filtered off and dried under reduced pressure (0.3 mm Hg) at 55° C. $N^2$-[N-(N-Lauroyl-L-alanyl)-γ-D-glutamayl]-meso-2-(L),6(D)-diaminopimelamic acid (0.75 g) is thus obtained.

Rf=0.38 [silica gel; n-butanol/pyridine/acetic acid/water (50/20/6/24 by volume)].

| Analysis | | | |
|---|---|---|---|
| calculated = | C = 56.72% | H = 8.64% | N = 12.25% |
| found = | 52.8% | 8.1% | 11.6% |

Sulphuric ash=6.9%.

After total hydrolysis, analysis on a Technicon autoanalyser shows the presence of the following aminoacids:
Ala=1.02 (theory=1)
Dap=0.96 (theory=1)
Glu=1.00 (theory=1)

$N^6$-Benzyloxycarbonyl-meso-2(L),6(D)-diaminopimelamic acid can be prepared in accordance with the process described in British patent specification No. 1496332.

EXAMPLE 9

Isobutyl chloroformate (0.65 cc) is added to a solution, kept at −5° C., of benzyl N-undecanoyl-L-alanyl-α-D-glutamate (2.383 g) in a mixture of tetrahydrofuran (100 cc) and triethylamine (0.7 cc). The mixture is stirred for 30 minutes at −5° C. and a solution, cooled to 0° C., of $N^6$-benzyloxycarbonyl-L,L/D,D-2,6-diaminopimelamic acid (1.617 g) in a mixture of 1N sodium hydroxide solution (5 cc) and water (50 cc) is then added. The reaction mixture is stirred for a few minutes at about 0° C. and then for 40 hours about 20° C. The reaction mixture is then acidified to pH 1 by adding 1N hydrochloric acid (10 cc). The tetrahydrofuran is evaporated off under reduced pressure (20 mm Hg) at 50° C. The concentrate contains a precipitate which is filtered off and washed 3 times with N/10 hydrochloric acid (60 cc in total) and water (20 cc). Drying under reduced pressure (0.3 mm Hg) at 20° C. yields a white solid (3.66 g) which is dissolved in acetic acid (20 cc) containing neutral silica gel (0.04–0.063 mm; 10 g). The mixture is concentrated to dryness under reduced pressure (20 mm Hg) at 50° C. and then introduced onto a column of diameter 3.5 cm, containing neutral silica gel (0.04–0.063 mm; 75 g). Elution is carried out successively with a mixture of ethyl acetate and cyclohexane (1/1 by volume; 600 cc), a mixture of ethyl acetate and cyclohexane (3/1 by volume; 600 cc), ethyl acetate (400 cc), a mixture of ethyl acetate and acetic acid (95/5 by volume; 600 cc), a mixture of ethyl acetate and acetic acid (9/1 by volume; 500 cc) and a mixture of ethyl acetate and acetic acid (85/15 by volume; 1,200 cc), 100 cc fractions being collected. Fractions 22 to 32 are combined and concentrated to dryness under reduced pressure (20 mm Hg) at 50° C. The resulting amorphous solid is taken up in diethyl ether (80 cc), triturated until it has all been converted to powder, filtered off and dried under reduced pressure (0.3 mm Hg). $N^2$-[$O^1$-Benzyl-N-(N-undecanoyl-L-alanyl)-γ-D-glutamyl]-$N^6$-benzyloxycarbonyl-L,L/D,D-2,6-diaminopimelamic acid (2.58 g) is thus obtained.

Rf=0.62 [silica gel; ethyl acetate/acetic acid (9/1 by volume)].

$N^2$-[$O^1$-Benzyl-N-(N-undecanoyl-L-alanyl)-γ-D-glutamyl]-$N^6$-benzyloxycarbonyl-L,L/D,D-2,6-diaminopimelamic acid (2.55 g) is dissolved in acetic acid (35 cc). Palladium-on-charcoal (containing 3% w/w of palladium; 2.55 g) is added and a slow stream of hydrogen is passed through the mixture for 2½ hours. The catalyst is filtered off and washed 3 times with aceticacid (30 cc in total). The filtrate is concentrated to dryness under reduced pressure (20 mm Hg) at 50° C. The amorphous solid is taken up in diethyl ether (50 cc), filtered off and dried under reduced pressure (20 mm Hg) at 20° C. $N^2$-[N-(N-Undecanoyl-L-alanyl)-γ-D-glutamyl]-L,L/D,D-2,6-diaminopimelamic acid (1.87 g) is thus obtained.

Rf=0.75 [silica gel; acetic acid].

Benzyl N-undecanoyl-L-alanyl-60-D-glutamate can be prepared in the following manner.

Isobutyl chloroformate (3.56 cc) is added to a solution, kept at −5° C., of undecanoic acid (5.1 g) in a mixture of tetrahydrofuran (140 cc) and triethylamine (3.84 cc). The mixture is stirred for 20 minutes at −5° C. and a solution, cooled to 0° C., of benzyl L-ananyl-α-D-glutamate hydrochloride (9.45 g) in a mixture of 1N sodium hydroxide solution (54.8 cc) and water (30 cc) is then added. The reaction mixture is stirred for 10 minutes at about −5° C. and then for 20 hours at about 20° C. The reaction mixture is then acidified to pH 1 by adding 1N hydrochloric acid (60 cc). The tetrahydrofuran is evaporated off under reduced pressure (20 mm Hg) at 50° C. The concentrate obtained is extracted twice with ethyl acetate (80 cc in total). The combined ethyl acetate phases are washed with water (40 cc) and dried over sodium sulphate. Filtration and concentration to dryness under reduced pressure (20 mm Hg) at 50 ° C. yields an oil (11.89 g) which is chromatographed on a column of diameter 4.5 cm, containing neutral silica gel (0.04–0.063 mm; 250 g). Elution is carried out with ethyl acetate, 100 cc fractions being collected. Fractions 3 to 5 are combined and concentrated to dryness under reduced pressure (20 mm Hg) at 20° C. to yield a pasty solid (5.85 g) which is chromatographed on a column of diameter 3.2 cm, containing neutral silica gel (0.04–0.063 mm; 115 g). Elution is carried out successively with a mixture of ethyl acetate and cyclohexane (1/1 by volume; 1 liter), ethyl acetate (1.7 liters) and a mixture of ethyl acetate and acetic acid (99/1 by volume; 600 cc), 100 cc fractions being collected. Fractions 11 to 30 are combined and concentrated to dryness under reduced pressure (20 mm Hg) at 50° C. Benzyl N-undecanoyl-L-alanyl-α-D-glutamate (2.47 g) is thus obtained in the form of a white solid.

Rf=0.71 [silica gel; ethyl acetate/acetic acid (9/1 by volume)].

EXAMPLE 10

Isobutyl chloroformate (0.69 cc) is added to a solution, kept at −5° C., of benzyl N-lauroyl-L-alan yl-α-D-glutamate (2.57 g) in a mixture of tetrahydrofuran (120 cc) and triethylamine (0.74 cc). The mixture is stirred for 20 minutes at −5° C. and a solution, cooled to 0° C., of $N^6$-benzyloxycarbonyl-L,L-2,6-diaminopimelamic acid (1.7 g) in a mixture of 1N sodium hydroxide solution (5.25 cc) and water (35 cc) is then added. The reaction mixture is stirred for 20 minutes at −3° C. and then for 22 hours at about 20° C. It is then acidified to pH 2 by adding 1N hydrochloric acid (20 cc). The precipitate formed is filtered off and washed 3 times with 0.1N hydrochloric acid (60 cc in total) and 3 times with water (60 cc in total). Drying in the atmosphere yields a white powder (3.97 g) which is chromatographed on neutral silica gel (0.04–0.063 mm; 200 g) contained in a column of diameter 3.8 cm.

Elution is carried out successively with ethyl acetate (600 cc), a mixture of ethyl acetate and acetic acid (95/5 by volume; 500 cc) and a mixture of ethyl acetate and acetic acid (9/1 by volume; 800 cc), 50 cc fractions being collected. Fractions 24 to 30 are combined and concentrated under reduced pressure (20 mm Hg) at 50° C. to yield an oil which is taken up in diethyl ether (100 cc) and triturated until it has all been converted to powder. The powder is filtered off and dried under reduced pressure (0.3 mm Hg).$N^2$-[$O^1$-Benzyl-N-(N-lauroyl-L-alanyl)-γ-D-glutamyl]-$N^6$-benzyloxycarbonyl-L,L-2,6-diaminopimelamic acid (1.24 g) is thus obtained.

Rf=0.85 [silica gel; n-butanol/pyridine/acetic acid/water (50/20/6/24 by volume)].

Rf=0.76 [silica gel; ethyl acetate/acetic acid (3/1 by volume)].

$N^2$-[N-(N-Lauroyl-L-alanyl)-γ-D-glutamyl]-L,L-2,6-diaminopimelamic acid can be prepared in the following manner: $N^2$-[$O^1$-Benzyl-N-(N-lauroyl-L-alanyl)-γ-D-glutamyl]-$N^6$-benzyloxycarbonyl-L,L-2,6-diaminopimelamic acid (1.36 g) is dissolved in acetic acid (40 cc). Palladium-on-charcoal (containing 3% w/w of palladium; 1.4 g) is added and a slow stream of hydrogen is passed through the mixture for 4 hours. After filtering and concentrating the filtrate under reduced pressure (20 mm Hg) at 55° C., an oil is obtained which is taken up in diethyl ether (100 cc) and triturated until it has all been converted to powder. The powder is filtered off and dried in air. $N^2$-[N-(N-Lauroyl-L-alanyl)-γ-D-glutamyl]-L,L-2,6-diaminopimelamic acid (0.96 g) is thus obtained.

Rf=0.38 [silica gel; n-butanol/pyridine/acetic acid/water (50/20/6/24 by volume)].

$N^6$-Benzyloxycarbonyl-L,L-2,6-diaminopimelamic acid can be prepared in the following manner:

Cupric bromide (2.14 g) dissolved in water (20 cc) is added to a solution of L,L-2,6-diaminopimelamic acid dihydrochloride (5 g) in water (15 cc), adjusted to pH 10 by the addition of 1N sodium hydroxide solution (45 cc). The reaction mixture is stirred for 2 hours at about 20° C. A small amount of insoluble material is filtered off and the filtrate is then cooled to a temperature between −3° C. and 0° C. Sodium bicarbonate (4.8 g) is added and benzyl chloroformate (4.1 cc) is then added dropwise in the course of 30 minutes. The reaction mixture is stirred for 18 hours at a temperature of the order 20° C. The blue precipitate formed is filtered off and washed 3 times with water (90 cc in total), 3 times with ethanol (90 cc in total) and 3 times with diethyl ether (90 cc in total). Drying under reduced pressure (20 mm Hg) at 50° C. yields the copper complex of $N^6$-benzyloxycarbonyl-L,L-2,6-diaminopimelamic acid (4.18 g) which is added to 1N hydrochloric acid (28 cc). The mixture is stirred for 1 hour at a temperature of the order of 20° C. An insoluble material is filtered off. Methanol (14 cc) is added to the filtrate and a stream of hydrogen sulphide is then passed through the mixture for 6 hours. The mixture is left to stand for 16 hours. The resulting black slurry is filtered and the solid is washed 3 times with water (15 cc in total). The combined filtrates are concentrated to a volume of 10 cc under reduced pressure (20 mm Hg) at 50° C., adjusted to pH 7 by adding triethylamine (5 cc) and then adjusted to pH 6.8 by adding 1N hydrochloric acid (5 cc). The white slurry thus obtained is kept at 0° C. for 2 hours. The product is filtered off and washed successively 3 times with water (30 cc in total), 3 times with ethanol (30 cc in total) and 3 times with diethyl ether (30 cc in total). After drying at 60° C. under reduced pressure (0.3 mm Hg), $N^6$-benzyloxycarbonyl-L,L-2,6-diaminopimelamic acid (1.78 g) is obtained.

$[\alpha]_D^{20} = +11°$ (c=1, 1N HCl).

Rf=0.45 [silica gel; n-butanol/pyridine/acetic acid/water (50/20/6/24 by volume)].

L,L-2,6-Diaminopimelamic acid dihydrochloride can be prepared in the following matter:

L,L-2,6-Dibenzyloxycarbonylaminopimelamic acid (17 g) is dissolved in a mixture of methanol (300 cc) and concentrated hydrochloric acid (d=1.19; 5.9 cc). Palladium-on-charcoal (containing 3% w/w of palladium; 17 g) is added and a stream of hydrogen is passed through the mixture for 4 hours. After filtering and concentrating the filtrate to dryness under reduced pressure (20 mm Hg) at 55° C., L,L-2,6-diaminopimelamic acid dihydrochloride (8.8 g) is obtained in the form of a hard foam.

L,L-2,6-dibenzyloxycarbonylaminopimelamic acid can be prepared in the following manner:

The monobenzyl ester of L,L-$N^2$,$N^6$-2,6-dibenzyloxycarbonyl-diaminopimelic acid (19 g) is dissolved in methanol (190 cc). The solution is cooled to about 0° C. and saturated with ammonia. As soon as it is saturated, it is transferred into a 1 liter autoclave. After this autoclave has been closed, it is kept for 6 days at about 20° C. After degassing, the solution thus obtained is concentrated under reduced pressure (20 mm Hg) at 50° C. The residue is dissolved in water (250 cc) and the resulting solution is adjusted to pH 2 by adding 4N hydrochloric acid (30 cc) and extracted 3 times with ethyl acetate (300 cc in total); the combined organic extracts are washed with a saturated solution of sodium chloride (100 cc), dried over sodium sulphate and concentrated to dryness under reduced pressure (20 mm Hg) at 50° C. L,L-2,6-dibenzyloxycarbonylaminopimelamic acid (17 g) is thus obtained in the form of an oil.

Rf=0.68 [silica gel; n-butanol/pyridine/acetic acid/water (50/20/6/24 by volume)].

The monobenzyl ester of L,L-$N^2$,$N^6$-2,6-dibenzyloxycarbonylaminopimelic acid can be prepared in the following manner:

Dibenzyl L,L-$N^2$,$N^6$-2,6-dibenzyloxycarbonyl-diaminopimelate (55 g) is dissolved in benzyl alcohol (400 cc) warmed to 40° C. A solution of 86% pure potassium hydroxide pellets (4.8 g) in benzyl alcohol (400 cc) is then run, in the course of 6½ hours, into this solution, and the mixture is kept at 40° C. for about 1 hour. The reaction medium is stirred at about 20° C. for a further 16 hours and then concentrated to dryness under reduced pressure (0.5 mm Hg) at 90° C. to yield an oil which is dissolved in water (1 liter). The solution obtained is extracted 3 times with ethyl acetate (900 cc in total). The aqueous phase extracted in this way is acidified to pH 2 by adding 4N hydrochloric acid (45 cc) and extracted 3 times with ethyl acetate (1.5 liters in total). The ethyl acetate phase thus obtained is washed with a saturated solution of sodium chloride (500 cc) and dried over anhydrous sodium sulphate. After filtering off the sodium sulphate, dicyclohexylamine (17 cc) is added and the mixture is concentrated to dryness under reduced pressure (20 mm Hg) at 40° C. to yield a yellow oil which is dissolved in ethanol (100 cc) to which water (100 cc) is added. After standing for 20 hours at 0° C. a white solid is obtained and this is filtered off, washed twice with water (100 cc in total) and taken up in a mixture of ethyl acetate (200 cc) and water (200 cc). The aqueous phase is acidified by adding a normal solution of methanesulphonic acid (40 cc). After decantation, the organic phase is washed twice with water (100 cc in total), dried over anhydrous sodium sulphate and concentrated to dryness under reduced pressure (20 mm Hg) at 50° C. The monobenzyl ester of L,L-$N^2,N^6$-2,6-dibenzyloxycarbonylaminopimelic acid (15 g) is thus obtained in the form of an oil.

Rf=0.76 [silica gel; n-butanol/pyridine/acetic acid/water (50/20/6/24 by volume)].

Dibenzyl L,L-$N^2,N^6$-2,6-dibenzyloxycarbonyldiaminopimelate can be prepared in the following manner:

A mixture of L,L-$N^2,N^6$-2,6-dibenzyloxycarbonylaminopimelic acid (44.7 g), p-toluenesulphonic acid (3 g), benzyl alcohol (30 cc) and toluene (300 cc) is introduced into a 500 cc three-necked flask fitted with a central stirrer and a Dean Stark apparatus. The reaction mixture is heated under reflux for 5 hours. Subsequently, after stirring for 16 hours at 20° C., the white insoluble material is filtered off and washed twice with a 5% w/v solution of sodium carbonate (400 cc in total) and twice with water (400 cc in total). After drying in the atmosphere, dibenzyl L,L-$N^2N^6$-2,6-dibenzyloxycarbonyldiaminopimelate (55.4 g), which melts at 118° C., is obtained.

Rf=0.53 [silica gel; acetic acid/ethyl acetate (8/2 by volume)].

L,L,$N^2,N^6$-2,6-dibenzyloxycarbonylaminopimelamic acid can be prepared in accordance with the method of A. Arendt et al., Roczniki Chemii Ann. Soc. Chim. Polonorum 48, 635 (1974).

EXAMPLE 11

Isobutyl chloroformate (0.91 cc) is added to a solution, kept at 0° C., of benzyl N-(3,5,5-trimethylhexanoyl)-L-alanyl-α-D-glutamate (3.14 g) in a mixture of tetrahydrofuran (150 cc) and triethylamine (0.98 cc). The mixture is stirred for 20 minutes at 0° C. and a solution, cooled to 0° C., of $N^6$-benzyloxycarbonyl-D,D/L, L-2,6-diaminopimelamic acid (2.263 g) in a mixture of 1N sodium hydroxide solution (7 cc) and water (70 cc) is then added. The reaction mixture is stirred for 1 hour at about 0° C. and then for 20 hours at about 22° C. A small amount of insoluble material is then removed by filtration and the filtrate is acidified to pH 1 by adding 1N hydrochloric acid (12 cc). The tetrahydrofuran is evaporated off under reduced pressure (20 mm Hg) at 50° C. The concentrate is extracted 3 times with ethyl acetate (150 cc in total). The combined ethyl acetate phases are washed with 0.1N hydrochloric acid (20 cc) and dried over sodium sulphate. Concentration to dryness under reduced pressure (20 mm Hg) at 50° C. yields an amorphous solid (5.14 g) which is defined is dissolved in a mixture of ethyl acetate and acetic acid (1/1 by volume; 60 cc) containing neutral silica gel (0.04–0.063 mm; 10 g). The mixture is concentrated to dryness under reduced pressure (20 mm Hg) at 50° C. and then introduced onto a column of diameter 3 cm, containing neutral silica gel (0.04–0.063 mm; 100 g). Elution is carried out successively with ethyl acetate (400 cc), a mixture of ethyl acetate and acetic acid (9/1 by volume; 200 cc), a mixture of ethyl acetate and acetic acid (8/2 by volume; 200 cc), a mixture of ethyl acetate and acetic acid (6/4 by volume; 160 cc) and a mixture of ethyl acetate and acetic acid (1/1 by volume; 240 cc), 40 cc fractions being collected. Fractions 15 to 25 are combined and concentrated to dryness under reduced pressure (20 mm Hg) at 50° C. The resulting oil is taken up in diethyl ether (50 cc) and triturated to a powder which is filtered off and dried under reduced pressure (0.3 mm Hg). $N^2$-{$O^1$-Benzyl-N-[N-(3,5,5-trimethylhexanoyl)-L-alanyl]-γ-D-glutamyl}-$N^6$-benzyloxycarbonyl-D,D/L,L-2,6-diaminopimelamic acid (2.85 g) is thus obtained.

Rf=0.32 [silica gel; ethyl acetate/acetic acid (3/1 by volume)]. $N^2$-{$O^1$-Benzyl-N-[N-(3,5,5-trimethylhexanoyl)-L-alanyl]-γ-D-gluramyl}-$N^6$-benzyloxycarbonyl-D,D/L,L-2,6-diaminopimelamic acid (2.76 g) is dissolved in acetic acid (100 cc). Palladium-on-charcoal (containing 3% w/w of palladium; 2.76 g) is added and a slow stream of hydrogen is passed through the mixture for 2½ hours. After filtering and concentrating the filtrate to dryness under reduced pressure (20 mm Hg) at 50° C., the oil is triturated in diethyl ether (50 cc) to yield a precipitate which is filtered off and dried under reduced pressure (0.3 mm Hg) at 20° C. $N^2$-{N-[N-(3,5,5-trimethylhexanoyl)-L-alanyl]-γ-D-glutamyl}-D,D/L,L-2,6-diaminopimelamic acid (2.07 g) is thus obtained.

Rf=0.32 [silica gel; n-butanol/pyridine/acetic acid/water (50/20/6/24 by volume)].

Rf=0.31 [silica gel; acetic acid].

Isobutyl chloroformate (4.3 cc) is added to a solution, kept at −6° C., of N-(3,5,5-trimethylhexanoyl)-L-alanine (7.59 g) in a mixture of tetrahydrofuran (400 cc) and triethylamine (4.63 cc). The mixture is stirred for 20 minutes at −6° C. and a solution, cooled to 3° C., of benzyl α-D-glutamate hydrochloride (9.06 g) in a mixture of 1N sodium hydroxide solution (66.2 cc) and water (14 cc) is then added. The reaction mixture is stirred for 15 minutes at about −5° C. and then for 66 hours at about 18° C.; it is then acidified to pH 1 by adding 1N hydrochloric acid (75cc). The tetrahydrofuran is evaporated off under reduced pressure (20 mm Hg) at 50° C. The concentrate is extracted 5 times with ethyl acetate (200 cc in total). The combined ethyl acetate phases are washed with 0.1N hydrochloric acid (40 cc) and dried over magnesium sulphate. Filtration and concentration to dryness under reduced pressure (20 mm Hg) at 50° C. yields an oil 14.8 g) which is dissolved in ethyl acetate (50 cc) containing neutral silica gel (0.04–0.063 mm; 30 g). The mixture is concentrated to dryness under reduced pressure (20 mm Hg) at 50° C. and then introduced onto a column of diameter 2.8 cm, containing neutral silica gel (0.04–0.063 mm; 280 g).

Elution is carried out successively with cyclohexane (2 liters), a mixture of cyclohexane and ethyl acetate (95/5 by volume; 1 liter), a mixture of cyclohexane and ethyl acetate (90/10 by volume; 1.5 liters), a mixture of cyclohexane and ethyl acetate 80/20 by volume; 5 liters), a mixture of cyclohexane and ethyl acetate (70/30 by volume; 1.5 liters) and a mixture of cyclohexane and ethyl acetate (50/50 by volume; 3.5 liters), 500 cc fractions being collected. Fractions 23 to 29 are combined and concentrated to dryness under reduced pressure (20 mm Hg) at 50° C. Benzyl N-(3,5,5-trimethylhexanoyl)-L-alanyl-α-D-glutamate (10.86 g) is thus obtained in the form of an oil which crystallises.

Rf=0.37 [silica gel; ethyl acetate].

N-(3,5,5-Trimethylhexanoyl)-L-alanine can be prepared in the following manner:

Isobutyl chloroformate (6.5 cc) is added to a solution, kept at −5° C., of 3,5,5-trimethylhexanoic acid (7.912 g) in a mixture of tetrahydrofuran (125 cc) and triethylamine (7 cc). The mixture is stirred for 20 minutes at −5° C. and a solution, cooled to 5° C., of L-alanine (4.495 g) in 1N sodium hydroxide solution (50 cc) is then added. The reaction mixture is stirred for 10 minutes at about 0° C. and then for 18 hours at about 25° C. The tetrahydrofuran is then evaporated off under reduced pressure (20 mm Hg) at 50° C. The concentrate is extracted twice with diethyl ether (40 cc in total) and acidified to pH 1 by adding 1N hydrochloric acid (55 cc). The oily precipitate which forms is extracted 5 times with ethyl acetate (250 cc in total). The ethyl acetate phases are combined, washed with a saturated solution of sodium chloride (25 cc) and dried over magnesium sulphate. Filtration and concentration to dryness under reduced pressure (20 mm Hg) at 50° C. yields an oil (11.79 g) which is dissolved in ethyl acetate (40 cc) containing neutral silica gel (b 0.063–0.20 mm; 20 g). The mixture is concentrated to dryness under reduced pressure (20 mm Hg) at 50° C. and then introduced onto a column of diameter 3 cm, containing neutral silica gel (0.063–0.20 mm; 120 g). Elution is carried out successively with cyclohexane (600 cc), a mixture of cyclohexane and ethyl acetate (95/5 by volume; 300 cc), a mixture of cyclohexane and ethyl acetate (90/10 by volume; 300 cc) a mixture of cyclohexane and ethyl acetate (80/20 by volume; 300 cc), a mixture of cyclohexane and ethyl acetate (50/50 by volume; 700 cc), ethyl acetate (300 cc) and a mixture of ethyl acetate and methanol (90/10 by volume; 300 cc), 100 cc fractions being collected. Fractions 17 to 28 are combined and concentrated to dryness under reduced pressure (20 mm Hg) at 45° C. This yields an oil (10.16 g) which is dissolved in diethyl ether (25 cc). The addition of petroleum ether (150 cc) yields an oil which is separated off by decantation. After drying in vacuo (0.2 mm Hg), N-(3,5,5-trimethylhexanoyl)-L-alanine (7.59 g) is obtained.

Rf=0.43 [silica gel; ethyl acetate].

EXAMPLE 12

Isobutyl chloroformate (0.56 cc) is added to a solution, kept at −5° C., of benzyl N-lauroyl-L-alanyl-α-D-glutamate (2.12 g) is a mixture of tetrahydrofuran (86 cc) and triethylamine (0.6 cc). The mixture is stirred for 30 minutes at −5° C. and a solution, cooled to 2° C., of $N^2$-t-butoxycarbonyl-D,D/L,L-2,6-diaminopimelamic acid (1.25 g) in a mixture of 1N sodium hydroxide solution (4.32 cc) and water (43 cc) is then added. The reaction mixture is stirred for a few minutes at about −5° C. and then for 18 hours at about 20° C. It is then acidified by adding a saturated solution of citric acid (50 cc). The tetrahydrofuran is evaporated off under reduced pressure (20 mm Hg) at 50° C. The concentrate obtained is extracted 5 times with ethyl acetate (200 cc in total). The combined ethyl acetate phases are washed with water (25 cc) and dried over sodium sulphate. Concentration under reduced pressure (20 mm Hg) at 50° C. yields an oil which is dissolved in a mixture of ethyl acetate (50 cc) and acetic acid (10 cc), containing neutral silica gel (0.04–0.063 mm; 10 g). The mixture is concentrated to dryness under reduced pressure (20 mm Hg) at 50° C. and then introduced onto a column of diameter 2 cm, containing neutral silica gel (0.04-0.063 mm; 50 g). Elution is carried out successively with ethyl acetate (200 cc), a mixture of ethyl acetate and acetic acid (95/5 by volume; 280 cc) and a mixture of ethyl acetate and acetic acid (9/1 by volume; 320 cc), 40 cc fractions being collected. Fractions 5 to 13 are combined and concentrated to dryness under reduced pressure (20 mm Hg) at 50° C. $N^6$-[$O^1$-Benzyl-N-(N-lauroyl-L-alanyl)-γ-D-glutamyl]-$N^2$-t-butoxycarbonyl-L,L/D,D-2,6-diaminopimelamic acid (2.23 g) is thus obtained in the form of an oil.

Rf=0.39 [silica gel; ethyl acetate/acetic acid (9/1 by volume)].

$N^6$-[$O^1$-Benzyl-N-(N-lauroyl-L-alanyl)-γ-D-glutamyl]-$N^2$-t-butoxycarbonyl-D,D/L,L-2,6-diaminopimelamic acid (2.19 g) is dissolved in a saturated anhydrous solution of hydrogen chloride in acetic acid (22 cc). The solution is left for 3 hours at 20° C. and the mixture is then concentrated to dryness under reduced pressure (20 mm Hg) at 50° C. $N^6$-[$O^1$-Benzyl-N-(N-lauroyl-L-alanyl)-γ-D-glutamyl]-D,D/L,L-2,6-diaminopimelamic acid hydrochloride (1.74 g) is thus obtained in the form of a partially crystalline oil.

Rf=0.47 [silica gel; n-butanol/pyridine/acetic acid/water (50/20/6/24 by volume)].

Rf=0.26 [silica gel; acetic acid].

$N^2$-t-Butoxycarbonyl-D,D/L,L-2,6-diaminopimelamic acid can be prepared in the following manner:

$N^2$-t-Butoxycarbonyl-$N^6$-benzyloxycarbonyl-D,D/L,L- 2,6-diaminopimelamic acid (4 g) is dissolved in acetic acid (100 cc). Palladium-on-charcoal (containing 3% w/w of palladium; 4 g) is added and a slow stream of hydrogen is passed through the mixture for 3 hours. The catalyst is filtered off and washed with acetic acid (10 cc) and the combined filtrates are concentrated to dryness under reduced pressure. (20 mm Hg) at 50° C. The oily residue thus obtained is triturated in diethyl ether (50 cc) until it has all been converted to powder. After filtration and drying, $N^2$-t-butoxycarbonyl-D,D/L,L-2,6-diaminopimelamic acid (3 g) in this obtained.

Rf=0.34 [silica gel; acetic acid].

EXAMPLE 13

{O$^1$-Benzyl-O$^5$-succinimido-N-[N-(2-n-pentyl-3-hydroxynonanoyl)-L-alanyl]}-D-glutamic acid (1 g) dissolved in 1,2-dimethoxyethane (10 cc) is added, in the course of 20 minutes, to a solution, kept at 8° C., of D,D/L,L-N$^6$benzyloxycarbonyl-2,6-diaminopimelamic acid (0.52 g) in a mixture of 1N sodium hydroxide solution (1.6 cc) and water (5 cc). The reaction medium is stirred for 24 hours at 20° C. and is then acidified to pH 1 by adding 1N hydrochloric acid (2 cc). After stirring for 3 hours at 20° C., the precipitate formed is filtered off, washed 3 times with water (30 cc in total) and dried under reduced pressure (20 mm Hg) at 20° C. to yield a white powder (1.1 g) which is chromatographed on a column of diameter 1.7 cm, containing neutral silica gel (0.04–0.063 mm; 22 g). Elution is carried out successively with ethyl acetate (110 cc), a mixture of ethyl acetate and acetic acid (95/5 by volume; 60 cc), a mixture of ethyl acetate and acetic acid (9/1 by volume; 180 cc) and acetic acid (80 cc), 10 cc fractions being collected. Fractions 24 to 38 are combined and concentrated to dryness under reduced pressure (20 mm Hg) at 60° C. The resulting amorphorus solid is taken up in diethyl ether (10 cc), filtered off and washed with diethyl ether (10 cc). After drying under reduced pressure (20 mm Hg) at 20° C., N$^2$-{O$^1$-benzyl-N-[N-(2-n-pentyl-3-hydroxynonanoyl)-L-alanyl]-γ-D-glutamyl}-N$^6$-benzyloxycarbonyl-D,D/L,L-2,6-diaminopimelamic acid (0.4 g) is obtained.

Rf=0.72 [silica gel; ethyl acetate/acetic acid (9/1 by volume)].

N$^2$-{O$^1$-Benzyl-N-[N-(2-n-pentyl-3-hydroxynonanoyl)-L-alanyl]-γ-D-glutamyl}-N$^6$-benzyloxycarbonyl-D,D/L,L-2,6-diaminopimelamic acid (0.4 g) is added to acetic acid (10 cc). Palladium-on-charcoal (containing 3% w/w of palladium; 0.4 g) is added and a slow stream of hydrogen is passed through the mixture for 1¼ hours. Filtering the reaction medium and concentrating the filtrate to dryness under reduced pressure (20 mm Hg) at 50° C. yields an oil which is taken up in diisopropyl ether (20 cc) and triturated until it has all been converted to powder, and the powder is filtered off. After drying under reduced pressure (20 mm Hg), N$^2$-{N-[N-(2-n-pentyl-3-hydroxynonanoyl)-L-alanyl]-γ-D-glutamyl}-D,D/L,L-2,6-diaminopimelamic acid (280 mg) is obtained.

Rf=0.39 [silica gel; n-butanol/pyridine/acetic acid/water (50/20/6/24 by volume)].

{O$^1$-Benzyl-O$^5$succinimido-N-[N-(2-n-pentyl-3-ydroxynonanoyl)-L-alanyl]}-D-glutamic acid can be prepared in the following manner:

Dicyclohexylcarbodiimide (7.4 g) dissolved in 1,2-dimethoxyethane (85 cc) is added, in the course of 10 minutes, to a solution, kept at 0° C., of benzyl N-(2-n-pentyl-3-hydroxynonanoyl)-L-alanyl-γ-D-glutamate (17.4 g) and N-hydroxysuccinimide (3.86 g) in 1,2-dimethoxyethane (170 cc). The reaction medium is stirred at 0° C. for 3½ hours and then kept at 4° C. for 16 hours. Acetic acid (2 cc) is then added thereto and the mixture is stirred for 1 hour at 20° C. The precipitate formed is filtered off and washed 3 times with 1,2-dimethoxyethane (75 cc in total). The filtrate is concentrated to dryness under reduced pressure (20 mm Hg) at 60° C. The concentrate is taken up in ethyl acetate (300 cc). After standing for 1 hour at 20° C., the precipitate formed is filtered off and washed twice with diisopropyl ether (50 cc in total). The filtrate is concentrated to dryness under reduced pressure (20 mm Hg) at 50° C. {O$^1$-Benzyl-O$^5$-succinimido-N-[N-(2-n-pentyl-3-hydroxynonanoyl)-L-alanyl]}-D-glutamic acid (22.8 g) is thus obtained in the form of an orange oil.

Rf=0.77 [silica gel; ethyl acetate].

Benzyl N-(2-n-pentyl-3-hydroxynonanoyl)-L-alanyl-α-D-glutamate can be prepared in the following manner:

Succinimide 2-n-pentyl-3-hydroxynonanoate (27.5 g) dissolved in 1,2-dimethoxyethane (644 cc) is added, in the course of 1 hour 10 minutes, to a solution, kept at 7° C., of benzyl L-alanyl-α-D-glutamate hydrochloride (27.8 g) in a mixture of water (245 cc) and triethylamine (22.9 cc). The reaction mixture is kept at 20° C. for 20 hours and then at 60° C. for 5 hours. The 1,2-dimethoxyethane is then evaporated off under reduced pressure (20 mm Hg) at 50° C.; the concentrate is acidified to pH 1 by adding 1N hydrochloric acid (150 cc) and extracted 5 times with ethyl acetate (1.5 liters in total). The combined ethyl acetate phases are washed 3 times with water (750 cc in total), dried over sodium sulphate and concentrated to dryness under reduced pressure (20 mm Hg) at 60° C. to yield an oil (38.6 g) which is dissolved in ethyl acetate (200 cc). Dicyclohexylamine (13 g) is added thereto. After standing for 20 hours at 4° C., the white solid formed is filtered off, washed twice with ethyl acetate (40 cc in total) and twice with diethyl ether (200 cc in total) and dried under reduced pressure (20 mm Hg) at 20° C. to yield a white powder (22.4 g) to which a product (1.9 g) obtained in a similar operation is added. The mixture is dissolved in water (500 cc); ethyl acetate (200 cc) and a saturated solution of citric acid (150 cc) are added to the aqueous solution. The organic phase is extracted twice with ethyl acetate (400 cc in total). The combined ethyl acetate phases are washed twice with water (200 cc in total), dried over sodium sulphate and concentrated to dryness under reduced pressure (20 mm Hg) at 60° C. Benzyl N-(2-n-pentyl-3-hydroxynonanoyl)-L-alanyl-α-D-glutamate (17.4 g) is thus obtained in the form of a beige paste.

Rf=0.25 [silica gel; ethyl acetate].

Succinimide 2-n-pentyl-3-hydroxynonanoate can be prepared in the following manner:

Dicyclohexylcarbodiimide (27 g) dissolved in 1,2-dimethoxyethane (300 cc) is added, in the course of 40 minutes, to a solution, kept at 0° C., of 2-n-pentyl-3-hydroxynonanoic acid (29.1 g) and N-hydroxysuccinimide (14.1 g) in 1,2-dimethoxyethane (300 cc). The reaction mixture is stirred at 0° C. for 3 hours and then kept at 4° C. for 21 hours. The precipitate formed is filtered off and washed twice with 1,2-dimethoxyethane (100 cc in total). The filtrate is concentrated to dryness under reduced pressure (20 mm Hg) at 50° C. The concentrate is taken up in a mixture of diisopropyl ether (300 cc) and acetic acid (3 cc). After standing for 2 hours at 20° C., the precipitate formed is filtered off and washed twice with diisopropyl ether (40 cc in total). The filtrate is concentrated to dryness under reduced pressure (20 mm Hg) at 50° C. Succinimide 2-n-pentyl-3-hydroxynonanoate (42.6 g) is thus obtained in the form of a yellow oil.

2-n-Pentyl-3-hydroxynonanoic acid can be prepared in accordance with the method of E. Lederer et al., Bull. Soc. Chim., 1952, 413.

EXAMPLE 14

A chloromethylated styrene/divinylbenzene copolymer (98/2; 150 g) containing 1 milliequivalent of chlorine per gram is added to a solution of N-α-t-butoxycarbonyl-N-ε-benzyloxycarbonyl-L-lysine (25 g) in ethanol (250 cc). The reaction medium is stirred for 3 minutes at 20° C., triethylamine (9.2 cc) is then added and the reaction medium is stirred for 48 hours at 78° C. The polymer is filtered off, washed successively 3 times with ethanol (750 cc in total) and 3 times with methylene chloride (750 cc in total) and then dried under reduced pressure (20 mm Hg) at 50° C. N-α-t-Butoxycarbonyl-N-ε-benzyloxycarbonyl-L-lysyl-polymer (160.9 g) is thus obtained.

D-Glutamic acid is attached to the L-lysyl-polymer derivative by carrying out the following sequence of operations in a reactor fitted with a stirrer and, at its base, with a fritted glass filter.

(1) The polymer is washed 3 times in succession with methylene chloride (3×100 cc). Each addition of solvent is followed by stirring for 3 minutes and then by draining.

(2) The t-butoxycarbonyl protecting group of the lysine is then removed by adding a mixture of trifluoroacetic acid and methylene chloride (1/1 by volume; 100 cc), stirring for 20 minutes and then draining.

(3) The polymer is then washed successively with
(a) methylene chloride (3×100 cc),
(b) methanol (3×100 cc) and
(c) methylene chloride (3×100 cc),
each addition of solvent being followed by stirring for 3 minutes and then by draining.

(4) The polymer is then neutralised by adding a mixture of methylene chloride and N-methylmorpholine (9/1 by volume; 100 cc), stirring for 10 minutes and then by draining.

(5) The polymer is then washed with methylene chloride (3×100 cc), each addition of solvent being followed by stirring for 3 minutes and then by draining.

(6) The following are then added in succession:
(a) a solution of benzyl N-t-butoxycarbonyl-α-D-glutamate (5.4 g) in methylene chloride (50 cc), with stirring for 10 minutes, and
(b) a solution of dicyclohexylcarbodiimide (3.3 g) in methylene chloride (50 cc), with stirring for 20 hours and then by draining.

(7) The polymer is washed successively with
(a) methylene chloride (3×100 cc),
(b) acetic acid (3×100 cc) and
(c) methylene chloride (3×100 cc),
each addition of solvent being followed by stirring for 3 minutes and then by draining.

N-α-(O$^1$-Benzyl-N-t-butoxycarbonyl-γ-D-glutamyl)-N-ε-benzyloxycarbonyl-L-lysyl-polymer is thus obtained.

Alanine is attached to the dipeptide-polymer by repeating operations 1, 2, 3, 4, 5, 6 and 7, modifying operation no. 6 as follows:

The following are added in succession:
(a) a solution of N-t-butoxycarbonyl-L-alanine (3.03 g) in methylene chloride (50 cc), with stirring for 10 minutes, and
(b) a solution of dicyclohexylcarbodiimide (3.3 g) in methylene chloride (50 cc), with stirring for 20 hours and draining.

N-α-[O$^1$-Benzyl-N-(N-t-butoxycarbonyl-L-alanyl)-γ-D-glutamyl]-N-ε-benzyloxycarbonyl-L-lysyl-polymer is thus obtained.

Palmitic acid is attached to the tripeptide-polymer by repeating operations 1, 2, 3, 4, 5, 6 and 7, modifying operation no. 6 as follows:

The following are added in succession:
(a) a solution of palmitic acid (4.2 g) in methylene chloride (50 cc), with stirring for 10 minutes, and
(b) a solution of dicyclohexylcarbodiimide (3.3 g) in methylene chloride (50 cc), with stirring for 20 hours and then draining.

N-α-[O$^1$-Benzyl-N-(N-palmitoyl)-L-alanyl)-γ-D-glutamyl]-N-ε-benzyloxycarbonyl-L-lysyl-polymer is thus obtained.

The polymer is suspended in trifluoroacetic acid (130 cc) contained in a reactor fitted with a stirrer and, at its base, with a fritted glass filter. A stream of hydrogen bromide is passed through this suspension for 90 minutes. The polymer is then drained and washed 3 times with acetic acid (300 cc in total), each addition of acetic acid being followed by stirring for 3 minutes and then by draining. The filtrates are combined and concentrated to dryness under reduced pressure (20 mm Hg) at 50° C. The oil thus obtained is taken up in ethyl acetate (50 cc). A precipitate forms and is filtered off and washed twice with diethyl ether (60 cc in total). It is hygroscopic and is dissolved in acetic acid (50 cc) containing neutral silica gel (0.04–0.063 mm; 7 g). The mixture is concentrated to dryness under reduced pressure (20 mm Hg) at 50° C. and the residue is introduced into a column of diameter 2.6 cm, containing neutral silica gel (0.04–0.063 mm; 70 g).

Elution is carried out successively with a mixture of ethyl acetate and acetic acid (9/1 by volume; 700 cc), a mixture of ethyl acetate and acetic acid (8/2 by volume; 1,700 cc), a mixture of ethyl acetate and acetic acid (7/3 by volume; 600 cc), a mixture of ethyl acetate and acetic acid (1/1 by volume; 2,400 cc), a mixture of ethyl acetate and acetic acid (2/8 by volume; 600 cc) and acetic acid (1,100 cc), 100 cc fractions being collected. Fractions 53 to 70 are combined and concentrated to dryness under reduced pressure (20 mm Hg) at 50° C. to yield an amorphous solid (1.28 g) which is dissolved in acetic acid (b 50 cc) containing neutral silica gel (0.04–0.063 mm; 2.4 g). The mixture is concentrated to dryness under reduced pressure (20 mm Hg) at 50° C. and the residue is introduced onto a column of diameter 1.5 cm, containing neutral silica gel (0.04–0.063 mm; 24 g). Elution is carried out successively with a mixture of ethyl acetate and acetic acid (7/3 by volume; 300 cc), a mixture of ethyl acetate and acetic acid (6/4 by volume, 150 cc), a mixture of ethyl acetate and acetic acid (1/1 by volume; 300 cc), a mixture of ethyl acetate and acetic acid (4/6 by volume; 250 cc), a mixture of ethyl acetate and acetic acid (3/7 by volume; 350 cc), a mixture of ethyl acetate and acetic acid (2/8 by volume; 350 cc), a mixture of ethyl acetate and acetic acid (1/9 by volume; 200 cc) and acetic acid (200 cc), 50 cc fractions being collected. Fractions 25 to 42 are combined and concentrated to dryness under reduced pressure (20 mm Hg) at 50° C. The resulting amorphous solid is taken up in ethyl acetate (30 cc), filtered off and washed with ethyl acetate (20 cc) and diethyl ether (20 cc). After drying under reduced pressure (0.3 mm Hg) at 50° C., N-α-[N-(N-palmitoyl-L-alanyl)-γ-D-glutamyl]-L-lysine (0.52 g) is obtained.

Rf=0.30 [silica gel; n-butanol/pyridine/acetic acid/water (50/20/6/24 by volume)].

| Analysis: | | | |
|---|---|---|---|
| calculated | C = 54.13 | H = 8.63% | N = 8.42% |
| found | = 54.9% | 8.6% | 8.7% |

Sulphuric ash=1.7%.

After total hydrolysis, analysis on a Technicon autoanalyser shows the presence of the following amino acids:
Ala 0.99 (theory=1)
Glu 1.00 (theory=1)
Lys 1.02 (theory=1)

The present invention includes within its scope pharmaceutical compositions which comprise at least one tripeptide of general formula II or non-toxic salt thereof, in association with one or more compatible and pharmaceutically acceptable carriers or diluents. These compositions can be used either as vaccine adjuvants or as non-specific stimulants of anti-infectious and antitumoral immunity.

When used as vaccine adjuvants, the compounds according to the invention are administered at the same time and by the same method as the antigen (viral, bacterial, parasitic or other antigen) against which it is desired to increase the cell immunity reactions (delayed-type hypersensitivity) or the production of circulating or local antibodies in the immunised subject (man or domestic animal).

The products are administered in relatively low doses (of the order of one mg) as a mixture with the antigen and by the same method (e.g. by the intramuscular, subcutaneous, intravenous, intranasal or oral method). If necessary, the compound according to the invention and the antigen can be emulsified in an appropriate oily excipient or incorporated into liposomes.

As non-specific immunostimulants, the compounds of the invention are administered in doses of from 0.1 to 500 mg/kg animal body weight by the parenteral method (intravenous, subcutaneous or intramuscular method) or by the intranasal, oral, rectal or, if appropriate, intratumoral method.

Solid compositions for oral administration include tablets, pills, powders and granules. In such solid compositions the active compound is admixed with at least one inert diluent such as sucrose, lactose or starch. The compositions may also comprise, as in normal practice, additional substances other than inert diluents, e.g. lubricating agents, such as magnesium stearate.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, sweetening and flavouring agents.

Preparations according to the invention for parenteral administration include sterile aqueous solutions, suspensions and emulsions. Examples of non-aqueous vehicles are propylene glycol, polyethylene glycol, vegetable oils such as olive oil, and injectable organic esters such as ethyl oleate. These compositions may also contain adjuvants in particular wetting agents, emulsifiers or dispersing agents. They may be sterilised by, for example, filtration through a bacteria-retaining filter, by incorporation in the compositions of sterilising agents, or by heating. They may also be manufactured in the form of solid compositions sterilised, e.g. by irradiation, which can be dissolved in sterile water or dispersed in any other sterile injectable medium before use.

Compositions for intranasal administration may be sterile aqueous solutions, suspensions or emulsions, which may if necessary be associated with a compatible propellant.

Compositions for rectal administration are suppositories which contain, in addition to the active substance, excipients such as cacao butter or a suitable wax base.

The following Examples illustrate pharmaceutical compositions according to the invention:

EXAMPLE 15

A solution which can be administered intravenously and has the following composition is prepared in accordance with the usual technique:

| | |
|---|---|
| $N^2$-(N-lauroyl-L-alanyl-$\gamma$-D-glutamyl)-D,D/L,L-2,6-diaminopimelamic acid | 0.5 g |
| injectable solution | 5 cc |

EXAMPLE 16

A solution which can be administered intravenously and has the following composition is prepared in accordance with the usual technique:

| | |
|---|---|
| methyl N-$\alpha$-[N-(N-lauroyl-L-alanyl)-$\gamma$-D-glutamyl]-L-lysinate | 0.5 g |
| injectable solution | 5 cc |

We claim:
1. A tripeptide of the general formula:

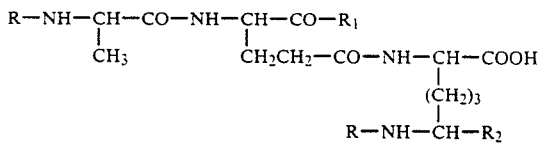

wherein the symbols R, which are the same or different, represent a hydrogen atom or a fatty acid residue, at least one of the symbols R representing a fatty acid residue, $R_1$ represents a hydroxy or amino radical, and $R_2$ represents a hydrogen atom or a carbamoyl radical, the alanine moiety is in the L form, the glutamic acid moiety is in the D form, the lysine moiety, when $R_2$ represents a hydrogen atom, is in the L form, and the 2,6-diaminopimelamic acid moiety, when the symbol $R_2$ represents a carbamoyl radical, is in the D,D, L,L, D,D,/L,L (racemic) or D,L (meso) form, or a non-toxic salt thereof.

2. A tripeptide according to claim 1 wherein $R_1$ represents a hydroxy radical, $R_2$ is as defined in claim 1, the symbol R bonded to the L-alanyl moiety is an alkanoyl radical containing 8 to 16 carbon atoms and the symbol R bonded to the amino group in the $\alpha$-position to the radical $R_2$ is a hydrogen atom or a non-toxic salt thereof.

3. A tripeptide according to claim 1 or 2 wherein $R_1$ represents a hydroxy radical, and $R_2$ represents a carbamoyl radical, or a non-toxic salt thereof.

4. A compound according to claim 1 which is N-$\alpha$-[N-(N-lauroyl-L-alanyl)-$\alpha$-D-glutamyl]-L-lysine.

5. A compound according to claim 1 which is $N^2$-(N-lauroyl-L-alanyl-α-D-glutamyl)-D,D/L,L-2,6-diaminopimelamic acid.

6. A compound according to claim 1 which is $N^2$-[N-(N-lauroyl-L-alanyl)-D-isoglutaminyl]-D,D/L,L-2,6-diaminopimelamic acid.

7. A compound according to claim 1 which is $N^2$-[N-(N-octanoyl-L-alanyl)-α-D-glutamyl]-D,D/L,L-2,6-diaminopimelamic acid.

8. A compound according to claim 1 which is $N^2$-[N-(N-palmitoyl-L-alanyl)-α-D-glutamyl]-D,D/L,L-2,6-diaminopimelamic acid.

9. A compound according to claim 1 which is a non-toxic salt of a tripeptide according to any one of claims 50 to 54.

10. A pharmaceutical composition useful as a vaccine adjuvant or as a non-specific stimulant of anti-infectious and antitumoral immunity which comprises an effective amount of a tripeptide according to claim 1 or a non-toxic salt thereof is association with a pharmaceutically acceptable carrier or diluent.

* * * * *

UNITED STATES PATENT AND TRADEMARK OFFICE
CERTIFICATE OF CORRECTION

PATENT NO. : 4,916,119
DATED : April 10, 1990
INVENTOR(S) : Jean Bouchaudon, et al.

It is certified that error appears in the above-identified patent and that said Letters Patent is hereby corrected as shown below:

Title page: item (73) Assignee should read--RHONE-POULENC SANTE LES MIROIRS--.

Signed and Sealed this

Tenth Day of November, 1992

Attest:

DOUGLAS B. COMER

Attesting Officer

Acting Commissioner of Patents and Trademarks